US009597303B2

(12) United States Patent
Cuevas Sànchez et al.

(10) Patent No.: US 9,597,303 B2
(45) Date of Patent: Mar. 21, 2017

(54) USE OF 2,5-DIHYDROXYBENZENE DERIVATIVES FOR TREATING DERMATITIS

(71) Applicant: AmDerma Pharmaceuticals, LLC, Bridgewater, NJ (US)

(72) Inventors: Pedro Cuevas Sànchez, Madrid (ES); Guillermo Gimenez Gallego, Madrid (ES); Inigo Saenz de Tejada Gorman, Madrid (ES); Javier Angulo Frutos, Valdemoro (ES); Serafin Valverde Lopez, Madrid (ES); Antonio Romero Garrido, Madrid (ES); Rosa Maria Lozano Puerto, Madrid (ES)

(73) Assignee: AmDerma Pharmaceuticals, LLC, Bridgewater, NJ (US)

( * ) Notice: Subject to any disclaimer, the term of this patent is extended or adjusted under 35 U.S.C. 154(b) by 0 days.

(21) Appl. No.: 14/863,896

(22) Filed: Sep. 24, 2015

(65) Prior Publication Data
US 2016/0008303 A1     Jan. 14, 2016

Related U.S. Application Data

(63) Continuation of application No. 14/333,729, filed on Jul. 17, 2014, now Pat. No. 9,192,592, which is a
(Continued)

(30) Foreign Application Priority Data

Aug. 16, 2006 (ES) .................................. 200602219
Jul. 2, 2007 (ES) .................................. 200701857

(51) Int. Cl.
*A61K 31/185* (2006.01)
*A61K 31/10* (2006.01)
(Continued)

(52) U.S. Cl.
CPC ............ *A61K 31/185* (2013.01); *A61K 8/466* (2013.01); *A61K 31/10* (2013.01); *A61K 31/192* (2013.01);
(Continued)

(58) Field of Classification Search
None
See application file for complete search history.

(56) References Cited

U.S. PATENT DOCUMENTS

| 3,954,767 A | 5/1976 | Esteve-Subirana |
| 4,115,648 A | 9/1978 | Esteve-Subirana |

(Continued)

FOREIGN PATENT DOCUMENTS

| EP | 0204987 | 12/1986 |
| EP | 1719509 | 11/2006 |

(Continued)

OTHER PUBLICATIONS

Kaur et al. An open trial of calcium dobesilate in patients with venous ulcers and statis dermatitis. International Journal of Dermatology, 2003, 42, 147-152.*
(Continued)

*Primary Examiner* — Anna Pagonakis
(74) *Attorney, Agent, or Firm* — Servilla Whitney LLC

(57) ABSTRACT

The present invention relates to the use of a 2,5-dihydroxybenzine derivative represented by Formula (I) or a pharmaceutically acceptable salt, solvate, isomer, or prodrug thereof for the therapeutic and/or prophylactic treatment of, inter alia, dermatitis.

15 Claims, 12 Drawing Sheets

Related U.S. Application Data continuation of application No. 13/209,803, filed on Aug. 15, 2011, now Pat. No. 8,815,836, which is a continuation of application No. 11/839,512, filed on Aug. 15, 2007, now abandoned.

(51) Int. Cl.

| | | |
|---|---|---|
| *A61K 31/192* | (2006.01) | |
| *A61K 31/60* | (2006.01) | |
| *A61K 31/618* | (2006.01) | |
| *A61K 8/46* | (2006.01) | |
| *A61K 31/222* | (2006.01) | |
| *A61K 45/06* | (2006.01) | |
| *A61Q 17/04* | (2006.01) | |
| *A61K 31/225* | (2006.01) | |

(52) U.S. Cl.
CPC .......... *A61K 31/222* (2013.01); *A61K 31/225* (2013.01); *A61K 31/60* (2013.01); *A61K 31/618* (2013.01); *A61K 45/06* (2013.01); *A61Q 17/04* (2013.01)

(56) References Cited

U.S. PATENT DOCUMENTS

| | | | |
|---|---|---|---|
| 4,137,311 | A | 1/1979 | Klein et al. |
| 4,837,378 | A | 6/1989 | Borgman |
| 4,970,202 | A | 11/1990 | Trigger |
| 5,519,018 | A | 5/1996 | Matusch |
| 5,698,595 | A | 12/1997 | Boelle et al. |
| 6,281,203 | B1 | 8/2001 | Touzan et al. |
| 6,664,406 | B1 | 12/2003 | Coupland et al. |
| 6,787,573 | B2 | 9/2004 | Nottet |
| 7,968,531 | B2 | 6/2011 | Cuevas Sanchez et al. |
| 8,101,660 | B2 | 1/2012 | Cuevas Sanchez et al. |
| 8,435,971 | B2 | 5/2013 | Cuevas Sanchez et al. |
| 8,497,257 | B2 | 7/2013 | Cuevas Sanchez et al. |
| 2002/0037319 | A1* | 3/2002 | Drizen ................ A61K 9/0014 424/488 |
| 2002/0143052 | A1 | 10/2002 | Lan-Hargest et al. |
| 2003/0216418 | A1 | 11/2003 | Stogniew et al. |
| 2004/0167222 | A1 | 8/2004 | Brooks et al. |
| 2005/0175559 | A1 | 8/2005 | DiNardo et al. |
| 2006/0258730 | A1 | 11/2006 | Allegretti et al. |
| 2007/0032471 | A1 | 2/2007 | Torrens Jover et al. |
| 2007/0149618 | A1 | 6/2007 | Cuevas Sanchez et al. |
| 2008/0114075 | A1 | 5/2008 | Cuevas Sanchez et al. |

FOREIGN PATENT DOCUMENTS

| | | |
|---|---|---|
| WO | WO-96/17589 | 6/1996 |
| WO | WO-96/25159 | 8/1996 |
| WO | WO-2005/013962 | 2/2005 |
| WO | WO-2005/077352 | 8/2005 |
| WO | WO-2006/029484 | 3/2006 |
| WO | WO-2006/069806 | 7/2006 |

OTHER PUBLICATIONS

Actinic Keratosis and Other Precancers, http//www.skincancer.org 2008, 3 pages.
Causes of Barrett's Esophagus, http://digestive-system.emedtv.com/barrett's-esophagus/causes-of-barrett's-esophagus.html Nov. 2006, 3 pages.
Catalogo de especialidades farmaceuticas, *Consejo General De Colegios Oficiales De Farmaceuticos* 1991, 4 pages.
Crohn's Disease Causes, http://cholitis.emedtv.com/crohn'sdisease/crohn's-disease-causes.html 2008, 3 pages.
Definition of Rosacea, *American Heritage Medical Dictionary,* www.freedictionary.com 2007, 6 pages.
Final Office Action in U.S. Appl. No. 13/209,803, mailed May 7, 2013, 12 pages.
Final Office Action in U.S. Appl. No. 11/839,512, mailed Jul. 1, 2010, 9 pages.
Glioma Brain Tumors, http://www.sfg.org/index.cfm?pagename=brainbriefings_fliomabrai tumors, 2008.
Non-Final Office Action in U.S. Appl. No. 13/209,803, mailed Feb. 5, 2014, 9 pages.
Non-Final Office Action in U.S. Appl. No. 13/209,803, mailed Nov. 29, 2012, 9 pages.
Non-Final Office Action in U.S. Appl. No. 11/839,512, mailed Feb. 15, 2011, 7 pages.
Non-Final Office Action in U.S. Appl. No. 11/839,512, mailed Oct. 6, 2009, 10 pages.
Non-Final Office Action in U.S. Appl. No. 11/839,512, mailed Dec. 22, 2008, 17 pages.
PCT International Search Report in PCT/ES2005/070017, mailed Jun. 22, 2005.
PCT International Search Report in PCT/EP2007/058438, mailed Nov. 27, 2007.
PCT International Search Report in PCT/EP2007/058440, mailed Feb. 22, 2008.
PCT International Written Opinion in PCT/ES2005/070017, mailed Jun. 22, 2005.
PCT International Written Opinion in PCT/EP2007/058438, mailed Nov. 27, 2007.
PCT International Written Opinion in PCT/EP2007/058440, mailed Feb. 22, 2008.
PCT International Search Report in WO-05/077352, mailed Jun. 22, 2005.
PCT International Search Report in WO-2008/020040, mailed Feb. 19, 2008.
PCT International Search Report in WO-2008/020039, mailed Jul. 15, 2008.
PCT International Search Report in WO-2008/020030, mailed Nov. 9, 2007.
PCT International Search Report in WO-2008/020028, mailed Nov. 14, 2007.
PCT International Search Report in WO-2008/020027, mailed Feb. 22, 2008.
PCT International Search Report in WO-2008/020042, mailed Dec. 6, 2007.
PCT International Search Report in WO-2008/020034, mailed Dec. 3, 2007.
PCT International Search Report in WO-2008/020033, mailed Nov. 30, 2007.
PCT International Search Report in WO-2008/020032, mailed Nov. 26, 2007.
PCT International Search Report in WO-2008/020031, mailed Nov. 28, 2007.
PCT International Search Report in WO-2008/020037, mailed Nov. 30, 2007.
PCT International Search Report in WO-2008/020036, mailed Nov. 28, 2007.
PCT International Search Report in WO-2008/020025, mailed Nov. 27, 2007.
Psoriasis Basic Facts—What is psoriasis, http://www.psoriasisguide.com/psus_basics/what is psoriasis.html, 2005.
Remington's Pharmaceutical Sciences, 1980, 7 pages.
Reply to the PCT Written Opinion in PCT/EP2007/058440.
Reply to the PCT Written Opinion in PCT/EP2007/058438.
What is Rosacea?, www.roacea.net, 2005.
Arhanic, V., et al., Attempts at Treating Rubeosis with Andioprotective Agents, Annals. of the Dr. M. Stojanovic Hospital, vol. 15, No. 2, 1976, 120-123.
Banker, Gilbert S., et al., *Modern Pharmaceutics*, 3rd Edition Marcel Dekker, Inc. 1996, 451 and 596.
Brannon, Heather, Atopic Dermatitis Treatment: Medications and Measures that can Improve Symptoms of Atopic Dermatitis, http://dermatology.about.com/cs/eczemadermatitis/a/atopictx.html, 2005, 2 pages.
Stasis dermatitis and ulcers, *MedlinePlus—U.S. National Library of Medicine* http://www.nlh.gov/midlineplus/ency/article/000834.htm, 2013, 3 pages.

(56) References Cited

OTHER PUBLICATIONS

Cuevas, Pedro, et al., Treatment of basal cell carcinoma with dobesilate, *J. Am. Acad. Dermatol.* Sep. 2005, 526-527.

Cuevas, Pedro, et al., Dobesilate in the treatment of plaque psoriasis, *Eur. J. Med. Res.*, vol. 10 2005, 373-376.

Divers, A.K., et al., Keratoacanthoma centrifugum marginatum: a diagnostic and therapeutic challenge, *Curtis*, vol. 73, No. 4 2004, Abstract, 257-262.

Dorwald, F. Z., Side Reactions in Organic Synthesis. A Guide to Successful Synthesis Design, *Wiley-VCH Verlag GmbH & Co.* 2005, 4 pages.

Goldman, Lee, et al., Principles of Cancer Therapy, *Cecil Textbook of Medicine*, vol. 1, W.B. Saunders Company 2000, 1060-1074.

Graber, R., et al., Calcium Dobesilate protects human peripheral blood mononuclear cells from oxidation and apoptosis, *Apoptosis*, vol. 3 1998, 41-49.

Hornick, J.L., et al., A New Chemically Modified Chimeric TNT-3 Monoclonal Antibody Directed Against DNA for the Radioimmunotherapy of Solid Tumors, Cancer Biotherapy & Radiopharmaceuticals, vol. 13, No. 4, 1998, 255-268.

Johnson, J.L., et al., Relationships between drug activity in NCI preclinical in vitro and in vivo models and early clinical trials, *British Journal of Cancer* 94(10) 2001, 1424-1431.

Jordan, V. C., Tamoxifen: A Most Unlikely Pioneering Medicine, *Nature Reviews Drug Discovery*, vol. 2 2003, 205-213.

Khawli, L.A., et al., Comparison of Recombinant Derivatives of Chimeric TNT-3 Antibody for the Radioimaging of Solid Tumors, Hybridoma and Hybridomics vol. 22 No. 1 2003, 1-10.

Kaur, Charandeep, et al., An open trial of calcium dobesilate in patients with venous ulcers and stasis dermatitis, *International Journal of Dermatology*, vol. 42 2003, 147-152.

Lameynardie, Stephanie, et al., Inhibition of choroidal angiogenesis by calcium dobesilate in normal Wistar and disbetic GK rats, *European Journal of Pharmacology*, vol. 510 2005, 149-156.

Lens, M., et al., Current clinical overview of cutaneous melanoma, *British Journal of Nursing*, vol. 17, No. 5 2008, Abstract, 2 pages.

Losa, Gabriele A., et al., Prevention of Oxidation and Apoptosis in Human Peripheral Blood Mononuclear Cells Exposed to Caldium Dobesilate, *International Journal of Angiology*, vol. 8 1999, 511-515.

Nour, A. F., et al., Preliminary Clinical Study with Calcium Dobesilate in Fibrocystic Disease of the Breast, *Acta Therapeutica*, vol. 12. No. 3 1986, 233-241.

Ruiz, Emilio, et al., Calcium Dobesilate Increases Endothelium-Dependent Relaxation in Endothelium-Injured Rabbit Aorta, *Pharmacological Research*, vol. 38, No. 5 1998, 361-366.

Rutkowski, Suzanne, Mystified by Your Medications?, *Asthma Magazine* 2001, 9-12.

Schulze, H. J., et al., Imiquimod 5% cream for the treatment of superficial basal cell carcinoma: results from a randomized vehicle-controlled phase III study in Europe, *British Journal of Dermatology*, vol. 152 2005, 939-947.

Sausville, Edward A., et al., Contributions of Human Tumor Xenografts to Anticancer Drug Development, *Cancer Res 66*(71) Apr. 1, 2006, 3351-3354.

Schon, Michael, et al., Psoriasis, *The New England Journal of Medicine* 2005, 1899-1912.

Sintov, Amnon C., et al., Percutaneous penetration and skin metabolism of ethylsalicylate-containing agent, TU-2100: in-vitro and in-vivo evaluation in guinea pigs, *Journal of Controlled Release*, vol. 79 2002, 113-122.

Stanwell, Caroline, et al., The Erbstatin Analogue Methyl 2,5-Dihydroxycinnamate Cross-Links Proteins and is Cytotoxic to Normal and Neoplastic Epithelial Cells by a Mechanism Independent of Tyrosine Kinase Inhibition, *Cancer Research*, vol. 55 1995, 4950-4956.

Stockfleth, E., et al., Successful treatment of actinic keratosis with imiquimod cream 5%: a report of six cases, *British Journal of Dermatology*, 144 2001, 1050-1053.

Takatsuka, Yoshikazu, et al., Various Analogues to Anthranilic Acid and Their Anti-Cancer Effects, *Mie Medical Journal*, vol. XVII, No. 1 1987, 11 pages.

Vippagunta, et al., *Advanced Drug Delivery Reviews*, vol. 48 2001, p. 18.

Wolff, Manfred E., Burger's Medicinal Chemistry and Drug Discovery, *Fifth Edition vol. 1: Principles and Practice* 1995, 4 pages.

Yamada, Katsuhisa, et al., Inhibitory Effect of Diacetyl Gentisic Acid on Melanogenesis, *Journal of Japanese Cosmetic Science Society*, vol. 22, No. 3 1998, 169-174.

\* cited by examiner

USE OF 2,5-DIHYDROXYBENZENE DERIVATIVES FOR TREATING DERMATITIS

CROSS-REFERENCE TO RELATED APPLICATIONS

This application is a Continuation of and claims the benefit of priority of pending U.S. application Ser. No. 14/333,729, filed on Jul. 17, 2014, which is a continuation of U.S. Pat. No. 8,815,836, issued on Aug. 26, 2014, which is a continuation of U.S. application Ser. No. 11/839,512, filed on Aug. 15, 2007, now abandoned, which claims the benefit of priority under 35 U.S.C. §119 of ES Application No. P200602219, filed Aug. 16, 2006 and of ES Application No. P200701857, filed Jul. 2, 2007. The foregoing applications, and all documents cited therein, are hereby incorporated herein by reference in their entirety.

FIELD OF THE INVENTION

The present invention relates to the use of 2,5-dihydroxybenzene derivatives to manufacture medicaments useful to prevent skin aging due to exposure to ultraviolet B rays (UVB), or to exposure to sun rays in general, to treat pathologies associated to said skin photoaging such as keratosis, as well as to treat dermatitis.

BACKGROUND OF THE INVENTION

Chronic exposure to ultraviolet B rays (UVB: 290-320 nm wavelength), or solar rays, in general (comprising, among other wavelengths, that of UVB radiation) produces skin aging (photoaging) due to the accumulation of DNA damage and on the structural proteins of the skin, evidencing in the form of fine wrinkles, laxity with loss of skin elasticity, elastosis, yellowish staining with localizad areas of melanin hyperpigmentation (solar, actinic or senile lentigo). Besides, skin photoaging is associated with the appearance of comedoes that are more evident in the "cutis romboidalis" at the rear part of the neck. In the histological test, an epidermic atrophy and degenerative changes in elastic fibers of the dermis may be observed (Pearse A D, Gaskell S A, Marks R. J Invest Dermatol 1987; 88 83-87; Berton T R, Mitchell D L, Fischer S M, Looniskar M F. J Invest Dermatol 1997; 109: 340-347). Furthermore, chronic exposure to UVB rays is a risk factor for the appearance of benign lesions, such as seborrheic keratosis, and premalignant lesions such as actinic keratosis (Kripke M L. Cancer Res 1994; 54: 6102-6105). Currently, there is no effective treatment for skin photoaging (Dermatol Surg. Special issue: Cosmeceuticals. Invited editors: Draelos Z D, Brody H J. 2005).

On the other hand, the hair follicle is the functional unit for hair elongation. Hirsutism is a clinical condition in which there in an excessive hair growth with an androgenic-type pattern (face, thorax, areolas, linea alba, lower part of the back, buttocks, limbs and external genitals) produced by an increase in the androgenic activity. Hypertricosis is a condition in which there is an excessive hair growth in areas sensitive and non-sensitive to androgens.

Obesity is a disease produced when the energy intake exceeds and produces an excess of adipose tissue. This process is regulated by the control on the intake, on the energy expenditure and efficiency and on the adipogenesis) (Gregoire F M. Exp Biol Med, 2001, 226: 997-1002; Palou A et al. Eur J Nutr, 2000, 39: 127-144). Prevention and/or treatment of obesity is as very important factor to reduce morbidity and mortality rates associated to cardiovascular disorders and to type 2 diabetes, which represent a high health and social cost in industrialized countries. Currently, there is no effective treatment for obesity. The effective therapies to treat obesity should interfere with the development of adipose tissue. To increase the adipose tissue mass, it is essential that preadipocytes are differentiated in a mature adipocyte phenotype. Besides morphological changes, the differentiation process of preadipocyte into adipocyte is accompanied by metabolic processes such as the capacity of storing energy in the form of triglycerides (McDougald O A, Lane M D. Annu Rev Biochem, 1995, 345-373; Spiegelman B M, Flier J S. Cell 1996, 87: 377-389). Therefore, the pharmacological inhibition of the differentiation of preadipocytes into adipocytes represents a therapeutic strategy to treat obesity.

There is a need to find alternative treatments to the current ones for skin aging and photoaging, both from the aesthetic and therapeutic points of view, based on the use of active principles.

SUMMARY OF THE INVENTION

Surprisingly, the inventors have found that 2,5-dihydroxybenzene derivatives, the pharmaceutically acceptable salts and solvates thereof, as well as isomers and prodrugs thereof are useful to prevent and/or therapeutically treat skin aging due to exposure to ultraviolet rays B (UVB), or to exposure to sun rays in general, to treat pathologies associated to said skin photoaging such as seborrheic keratosis. In addition said derivatives are useful to prevent and/or therapeutically treat dermatitis.

In certain embodiments, the invention provides a method for the treatment or prophylaxis of dermatitis, comprising administering to a subject in need thereof, an effective amount of a 2,5-dihydroxybenzene derivative represented by Formula (I) or a pharmaceutically acceptable salt, solvate, isomer, or prodrug thereof, wherein the compound of Formula (I) is:

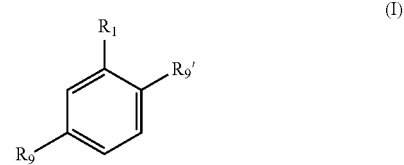

wherein:
$R_1$ is —$(CH_2)_a$Y or —CH=CH—$(CH_2)_p$Z;
Y is —$SO_3H$, —$SO_3^-$.$X^+$, —$SO_3R_3$, —$PO_3H$, —$PO_3$—.$X^+$, or 13 $PO_3R_3$, wherein when Y is —$SO_3H$, —$SO_3^-$.$X^+$ or —$SO_3R_3$, then $R_9$ and $R_{9'}$ are independently selected from —OH and —$OR_2$, wherein at least one of $R_9$ and $R_{9'}$ is a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group;
Z is —$SO_3H$, —$SO_3^-$.$X^+$, —$SO_3R_3$, —$PO_3H$, —$PO_3$—.$X^+$, —$PO_3R_3$, —$CO_2H$, —$CO_2^-$.$X^+$ or —$CO_2R_3$;
$X^+$ is an organic cation or an inorganic cation, such that the general charge of the compound is neutral;
$R_9$ and $R_{9'}$ are independently selected from —OH and —$OR_2$, wherein when $R_9$ and $R_{9'}$ are both —$OR_2$, then said $R_9$ and $R_{9'}$ can be the same or different;

$R_2$ is a substituted or unsubstituted alkyl group, a substituted or unsubstituted aryl group, a substituted or unsubstituted alkylsulfonyl group, a substituted or unsubstituted arylsulfonyl group, a substituted or unsubstituted alkylcarbonyl group or a substituted or unsubstituted arylcarbonyl group;

$R_3$ is a substituted or unsubstituted alkyl group or a substituted or unsubstituted aryl group;

a is a number selected from 0, 1, 2, 3, 4, 5 and 6; and p is an integer selected from 0, 1, 2, 3, 4, 5 and 6.

In certain embodiments, $R_1$ is —$(CH_2)_a$ Y or —CH=CH—$(CH_2)_p$ Y. In other embodiments, Y is selected from —$SO_3H$, —$SO_3^-.X^+$, —$SO_3R_3$. In yet other embodiments, $R_3$ is selected from methyl and ethyl. In some embodiments, $R_9$ and $R_{9'}$ are, independently, a or substituted unsubstituted alkylsulfonyloxy group, a substituted or unsubstituted arylsulfonyloxy group, substituted or unsubstituted alkylcarbonyloxy group or a substituted or unsubstituted arylcarbonyloxy group. In some embodiments, $R_2$ is selected from methylcarbonyl, phenylsulfonyl, 4-methylphenylsulfonyl, benzylsulfonyl, benzyl and phenyl In certain embodiments, the compound of Formula (I) is selected from the group consisting of: S-hydroxy-2-{[(4-methylphenyl)sulfonyl]oxy}benzenesulfonic acid; 2-hydroxy-5-{[(4-methylphenyl)sulfonyl]oxy}benzenesulfonic acid; 2,5-bis{[(4-methylphenyl)sulfonyl]oxy}benzenesulfonic acid; 2-(acetyloxy)-5-hydroxybenzenesulfonic acid; 5-(acetyloxy)-2-hydroxybenzenesulfonic acid; 2,5-bis(acetyloxy)benzenesulfonic acid; 5-hydroxy-2-{[(4-methylphenyl)sulfonyl]oxy}benzenehomosulfonic acid; 2-hydroxy-5-{-[(4-methylphenyl)sulfonyl]oxy}benzenehomosulfonic acid; acid; 2,5-bis{[(4-methylphenyl)sulfonyl]oxy}benzenehomosulfonic acid; 2-(acetyloxy)-5-hydroxybenzenesulfonic acid; 5-(acetyloxy)-2-hydroxybenzenehomosulfonic acid; 2,5-bis(acetyloxy)benzenehomosulfonic acid; 3-(2,5-dihydroxyphenyl)-2-propenoic acid (2,5-dihydroxycinnamic acid); 3-(5-hydroxy-2-{[(4-methylphenyl)sulfonyl]oxy})phenyl)-2-propenoic acid; 3-(2-hydroxy-5-{[(4-methylphenyl)sulfonyl]oxy})phenyl)-2-propenoic acid; 3-(2,5-bis{[(4-methylphenyl)sulfonyl]oxy}phenyl)-2-propenoic acid; 3-(2-(acetyloxy)-5-hydroxyphenyl)-2-propenioc acid; 3-(5-(acetyloxy)-2-hydroxyphenyl)-2-propenoic acid; 3-(2,5-bis(acetyloxy)phenyl)-2-propenoic acid; 3-(2-(benzyloxy)-5-hydroxyphenyl)-2-propenoic acid; bis(acetyloxy)phenyl)-2-propenoic acid; 3-(2-(benzyloxy)-5-hydroxyphenyl)-2-propenoic acid; 3-(5-(benzyloxy)-2-hydroxyphenyl)-2-propenoic acid; 3-(2,5-bis(benzyloxy)phenyl)-2-propenoic acid; and pharmaceutically acceptable salts, solvates, and prodrugs thereof.

In certain embodiments, the compound of Formula (I) is selected from: 2-(acetyloxy)-5-hydroxybenzenesulfonic acid, 5-(acetyloxy)-2-hydroxybenzenesulfonic acid and 2,5-bis(acetyloxy)benzenesulfonic acid.

In certain embodiments, the invention provides a method for the treatment or prophylaxis of dermatitis, wherein the dermatitis is selected from the group consisting of actinic dermatitis, allergic contact dermatitis, atopic dermatitis, carcinomatous dermatitis, contact dermatitis, diaper dermatitis, stasis dermatitis, neurodermatitis, dermatomyositis and radiation-induced dermatitis.

Advantageously, a compound of Formula (I) is administered topically. In certain embodiments, the compound of Formula (I) is administered orally, buccally, transdermally, by inhalation, or otically.

In certain embodiments, the invention provides a method for the treatment or prophylaxis of dermatitis further comprising administration of at least one additional therapeutic agent.

Examples of suitable additional therapeutic agents include diclofenac, T4 endonuclease, isotretinoin, acitretin, cidofoir, a corticostoroid, an antibiotic, an analgesic, an immunomodulator, including oral immunomodulator such as tacrolimus and pimecrolimus, and topical immunomodulators; an immunosuppressant, an anti-angiogenic, including anti-VEGF, anti-FGF and anti-EGF and anti-HGF; a leukotriene modifier, an aminosalicylate, an anesthetic, a non-steroidal anti-inflammatory, a modifier of a solubilized interleukin receptor, an inhibitor of a tyrosine-kinase receptor, a protein kinase C inhibitor, and a combination of two or more thereof.

In certain embodiments, the invention provides for administration of a compound of Formula (I) for the treatment and/or prophylaxis of dermatitis, wherein the compound is administered at least once per week. In other embodiments, the compound is administered at least once per day or at least twice per day.

In certain embodiments, a compound of Formula (I) is present in a pharmaceutical composition in an amount of at least about 1% w/w. In other embodiments, the compound is present in a pharmaceutical composition in an amount of at least about 2.5% w/w, at least about 5% w/w, at least about 10% w/w, or at least about 15% w/w.

In yet other embodiments, a compound of Formula (I) is administered over a period of at least about one week. In certain embodiments, the compound is administered over a period of at least about four weeks.

These and other aspects of the present invention are described in detail herein.

DETAILED DESCRIPTION OF THE INVENTION

Figure 1:
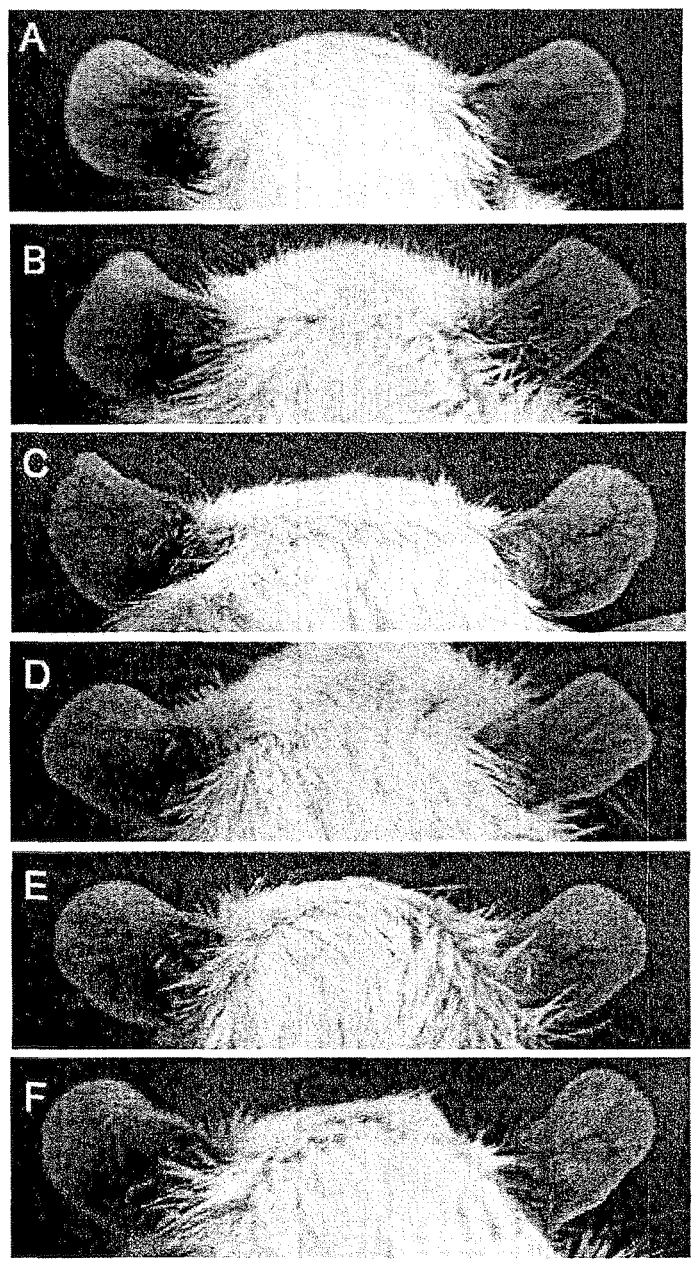
FIG. 1. Inhibitory effect of 2,5-dihydroxybenzenesulfonic acid (DHBS) on dermatitis induced by the application of benzalkonium chloride on the rat ears. Dermatitis was induced in both ears, and only the right ear was treated topically with a cream containing 5% DHBS; the left ear was used as control. The intravenous injection of Evans blue dye revealed the extent of dermatitis in the ears. The application of the cream containing DHBS remarkably reduced dye extravasation caused by the dermatitis, as shown in photographs (A-F) of the treated ears in the 6 rats that, 4 hours after dermatitis induction, exhibited a colored extent lower than untreated ears.

The definitions of the terms and the chemical groups comprised in the formulas herein are as follows:

The term "patient" refers to animals, preferably mammals, and more preferably humans, and includes males and females, children and adults.

The expression "effective amount" refers to the amount of compound and/or composition effective to achieve the desired purpose.

The terms "treat" or "treatment" refer to the prophylactic use of compounds or compositions of the present invention to avoid the symptoms of the disease or condition, or the therapeutical use to improve an existing condition.

"Alkyl" refers to a linear or branched chain hydrocarbon radical comprising carbon atoms and hydrogen, with no unsaturations, with one to twelve, preferably one to eight, more preferably one to six carbon atoms, bound to the rest of the molecule by a single bond, for example, methyl, ethyl, n-propyl, i-propyl, n-butyl, t-butyl, n-pentyl, etc.

"Alkenyl" refers to a linear or branched chain hydrocarbon radical comprising carbon atoms and hydrogen atoms, containing at least one unsaturation, with two to twelve, preferably two to eight, more preferably two to six carbon atoms, hound to the rest of the molecule by a single bond.

"Cycloalkyl" refers to a saturated carbocyclic ring having between three and eight, preferably three to six carbon atoms. They may exhibit a bridged structure. Suitable cycloalkyl groups include, but are not limited to, cycloalkyl groups such as cyclopropyl, cyclobutyl, cyclopentyl or cyclohexyl.

"Alkynyl" refers to a linear or branched chain hydrocarbon radical comprising carbon atoms and hydrogen, containing at least one triple carbon-carbon bond, whether conjugated or not, with two to twelve, preferably two to eight, more preferably two to six carbon atoms, bound to the rest of the molecule by a single bond such as —CCH, —CH$_2$CCH, —CCCH$_3$, —CH$_2$CCCH$_3$.

"Aryl" refers to an aromatic hydrocarbon radical containing from six to ten carbon atoms such as phenyl or naphthyl.

"Aralkyl" refers to an aryl group bound to the rest of the molecule by an alkyl group such as benzyl and phenetyl.

"Heterocycle" refers to a stable 3 to 15-membered, ring comprised of carbon atoms and between one and five heteroatoms selected from the group consisting of nitrogen, oxygen and sulfur, preferably a 4 to 8-membered ring with two, three or four heteroatoms, more preferably a 5 or 6-membered ring with one, two or three heteroatoms. For the purpose of the present invention, the heterocycle may be a monocyclic, bicyclic or tricyclic ring system that may include fused ring systems; bridged structures; and the nitrogen, carbon or sulfur atoms in the heterocyclic radical may be optionally oxidized; the nitrogen atom may be optionally quaternized; and the heterocyclic radical may be partially or completely saturated or it may be aromatic. Examples of such heterocycles include, but are not limited to, azepines, benzimidazole, benzothiazole, furan, isothiazole, imidazole, indole, piperidine, piperazine, quinoline, thiadiazol, tetrahydrofuran.

Unless otherwise specified, the alkyl, cycloalkyl, alkenyl, alkynyl, aryl, aralkyl and heterocycle radicals may be optionally substituted by one, two or three substituents such as halo, alkyl, alkenyl, alkynyl, aryl, cycloalkyl, hydroxy, alkoxy, sulfoxy, O-Benzyl, O-Benzoyl, carboxyl, alkylcarboxyl, arylcarboxyl, alkylcarbony, arylcarbonyl, cyano, carbonyl, acyl, alkoxycarbonyl, amino, alkylamino, dialkylamino, arylamino, diarylamino, alkylarylamino, alkylsulphinyl, amidyl, carbamoyl, sulfonamido, nitro, nitrite, nitrate, thionitrate and carboxamido.

The term "alkoxycarbonyl" refers to a compound having the formula —C(=O)O—, where the C-terminal is bound to the molecule and the O-terminal is hound to a carbon atom to form an ester function. Said carbon atom may be part of an alkyl, alkenyl, cycloalkyl, alkynyl, aryl, aralkyl or heterocyclic group.

The term "alkoxycarbonylalkyl" refers to a compound of the previously defined formula —C(=O)O—, wherein the C-terminal binds to a molecule through an alkyl group. The terms "aryloxy- aryialkoxy- or alkylaryloxy-carbonylalkyl" will be understood similarly to "alkoxycarbonylalkyl".

The term "arylalkyl" refers to an aryl radical, as defined herein, hound to an alkyl radical, as defined herein. The exemplary arylalkyl groups include benzyl, phenylethyl, 4-hydroxybenzyl, 3-fluorobenzyl, 2-fluorophenylethyl and the like.

The term "alkylaryl" refers to an alkyl group, as defined herein, to which an aryl group is bound, as defined herein. The exemplary alkylaryl groups include benzyl, phenylethyl, hydroxybenzyl, fluorobenzyl, fluorophenylethyl, and the like.

The term "alkylsulfonyl" refers to a $R_{50}$—S(O)$_2$—, wherein $R_{50}$ is a lower alkyl group, as defined herein.

The term "arylsulfonyl" refers to a $R_{55}$—S(O)$_2$— wherein $R_{55}$ is an aryl group, as defined herein.

The term "alkylsulphinyl" refers to a $R_{55}$—S(O)$_2$—, wherein $R_{55}$ is an aryl group, as defined herein.

The term "arylsulphinyl" refers to a $R_{55}$—S(O)$_2$—, wherein $R_{55}$ is an aryl group, as defined herein.

The term "sulfonamide" refers to a —S(O)$_2$—N($R_{51}$)($R_{57}$), wherein $R_{51}$ and $R_{57}$ are each independently a hydrogen atom, an alkyl group, an aryl group, heterocycle, as defined herein, or else $R_{51}$ and $R_{57}$ together form a heterocyclic ring, a cycloalkyl group or a bridged cycloalkyl group, as defined herein.

The term "alkylsulfonamide" refers to a sulfonamido group, as defined herein, bound to an alkyl group, as defined herein.

The term "arylsulfonamide" refers to a sulfonamide group, as defined herein, bound to an aryl group, as defined herein.

The term "alkylcarbonyl" refers to a $R_{52}$—C(O)$_2$—, wherein $R_{52}$ is an alkyl group, as defined herein.

The term "arylcarbonyl" refers to the $R_{55}$—S(O)$_2$— radical, wherein R55 is an aryl group, as defined herein.

The term "carboxamide" refers to a —C(O)N($R_{52}$)($R_{58}$) radical, wherein $R_{52}$ and $R_{58}$ are each independently a hydrogen atom, an alkyl group, an aryl group or an heterocyclic group, as defined herein or else $R_{51}$ and $R_{57}$ together form an heterocyclic ring, a cycloalkyl group, or a bridged cycloalkyl group, as defined herein.

The term "carboxylic ester" refers to —C(O)O$R_{59}$, wherein $R_{59}$ is an alkyl group an aryl group or an heterocyclic group, as defined herein.

The term "alcoxyalkyl" refers to an alcoxy group, as defined herein, bound to an alkyl group, as defined herein. Examples of alcoxyalkyl groups are methoxymethyl, methoxyethyl, isopropoximethyl and the like.

The term "amine" refers to any organic compound containing at least one basic nitrogen atom.

The term "organic cation" refers to a positively charged organic ion. The exemplary organic cations include ammonium cations unsubstituted or substituted with alkyl, primary, secondary o tertiary amines, alkylamines, arylamines, cyclic amines, N,N'-dibenzylethylenediamine, and the like.

The term "inorganic cation" refers to a positively charged metal ion. The exemplary inorganic cations include Group I metal cations such as sodium, potassium, magnesium, calcium and the like.

The term "prodrug" refers to compounds that rapidly convert in vivo into pharmacologically active compounds. Prodrug design is generally studied in Hardma et al. (eds.), Goodman and Gilman's The Pharmacological Basis of Therapeutics, 9th ed., pages 11-16 (1996). A thorough study is presented in Higuchi et al., Prodrugs as Novel Delivery Systems, vol. 14, ASCD Symposium Series, and in Roche (ed.), Bioreversible Carriers in Drug Design, American Pharmaceutical Association and Pergamon Press (1987).

The term "ester derivative of a compound of formula (I)" refers to the compound of formula (I) wherein at least one of $R_9$ and $R_{9'}$ is an ester group. For example, the ester derivative of 2,5-dihydroxybezene sulfonic acid or dobesilate ester derivative refers to the compound 2,5-dihydroxybezene sulfonic acid (dobesilate) wherein at least one of the hydroxyl groups has been esterified.

The term "ester of a compound of formula (I)" refers to an ester of the sulfonic or carboxylic acid group at position 1. For example, the ester of 2,5-dihydroxybenzensulfonic acid or ester of dobesilate refers to an ester of the sulfonic acid group at position 1.

The compounds of the invention having one or more asymmetric carbon atoms may exist as optically pure enantiomers, pure diastereomers, mixtures of enantiomers, mixtures of diastereomers, racemic mixtures of enantiomers, diastereomeric racemates or mixtures of diastereomeric racemates. It should be clearly understood that the invention contemplates and includes these isomers and mixtures thereof within its scope.

The term "topical" refers to the administration of a compound by applying it on the body surface and includes, but is not limited to, transdermal administration and administration through the mucosa.

The term "transdermal" refers to the delivery of a compound that enters into the bloodstream through the skin.

The expression "through the mucosa" refers to the delivery of a compound that enters into the bloodstream through the mucous tissue.

The term "parenteral" refers to the administration of a compound by means of a subcutaneous, intravenous, intramuscular, intracardiac, intradermal, intraperitoneal, intrathecal or intrasternal injection; and also includes local or systemic infusion techniques.

The expression "penetration enhancement" or "permeation enhancement" refers to the increase in the permeability of the skin or mucous tissue to a pharmacologically active compound selected in such a way that it increases the penetration rate through the skin or mucous tissue.

"Excipients" or "vehicles" refers to the vehicle materials suitable for compound administration and include any such material known in the art such as, for example, any liquid, gel, solvent, liquid diluent, solubilizer, or the like, which is non-toxic and which does not show harmful interaction with any component of the composition.

The expression "sustained release" refers to the release of an active compound and/or composition such that the blood levels of the active compound are maintained within a desirable therapeutic range over a period of time. The sustained release formulation may be prepared using any conventional known method by a skilled in the art in order to obtain the desired release characteristics.

The term "Dermatitis" refers to a inflammatory skin disease.

"Atopic dermatitis" refers to a chronic disease affecting the skin. Atopic dermatitis is produced by a combination of genetic and environmental factors and associated with excessive IgE antibody formation.

"Contact dermatitis" refers to an inflammation of the skin that is induced by external contact with substances that damage the skin by direct chemical action or through an immunological mechanism. Contact dermatitis is associated with lesions produced on the skin upon contacting an antigen or irritating solution.

"Stasis dermatitis" refers to a dermatitis in which stasis is merely one factor in eczema of the lower leg; edema of nutritional or other origin, infection, and reaction to topical medicaments are important factors.

"Actinic dermatitis" or "photodermatitis" refer to dermatitis provoked by exposure to sunlight.

"Neurodermatitis" refers to a skin disorder of psychosomatic genesis or in which psychological factors play an important part, as when rubbing and scratching induce circumscribed patches of thickened skin.

"Allergic contact dermatitis" refers to an acute inflammatory condition of the skin following topical exposure to an allergen to which the subject shows delayed hypersensitivity.

"Carcinomatous dermatitis" refers to an inflammatory alteration of the skin due to underlying carcinoma.

"Diaper dermatitis" refers to any eruption occurring in the skin that is usually covered by the diaper and is often induced by prolonged contact with urine or feces.

The term "dermatomyositis" refers to a collagen vascular disease characterized by skeletal muscle inflammation and by erythema and edema of the skin, notably on the eyelids, backs of the hands, and the extensor aspects of the limbs.

"Seborrheic keratosis" refers to non-cancerous growth of the external layer of the skin.

The term "therapeutic agent" includes any active agent that can be used to treat or prevent a disease described herein. "Therapeutic agents" include but are not limited to immunomodulatory treatments, such as a tacrolimus ointment or a pimecrolimus cream and the like; topical corticosteroids (cream, unguents, ointments or gels) or systemic corticosteroids; topical or systemic immunosupressants, such as, for example, cyclosporine, metrotrexate, azathioprine, and the like; phototherapy; emollients such as for example, white petrolatum, eucerin, urea cream, mineral oil, aluminum acetate, and the like; barrier creams, such as, for example, zinc oxide paste, and the like; moisturizing agents, such as, for example, menthol, camphor, and the like; local anesthetics, such as, for example, lidocaine, and the like; topical corticoids, such as, for example, triamcinolone acetate, and the like; systemic corticoids, such as, for example, prednisone, and the like; antihistamines, such as, for example, diphenhydramine, hydroxyzine, and the like; podophylline resin, locally applied; cantharin, only combined with podophyllins; salicylic acid, locally applied; imiquimod; bleomycin; exfoliating agents, such as, for example, alpha hydroxy acids (glycolic acid, salicylic acid, lactic acid), trichloroaectic, phenols (carbolic acid, croton oil, and the like; diclofenac gel; 5-fluorouracyl, bleaching agents and photoprotectors, and the like. A therapeutic agent includes pharmaceutically acceptable salts thereof, prodrugs and pharmaceutical derivatives thereof.

In a first aspect, the present invention relates to the use of a compound of Formula (I) or a pharmaceutically acceptable salt or solvate, isomer or prodrug thereof to prepare a drug for the cosmetic, therapeutic and/or prophylactic treatment of dermatitis or seborrheic keratosis, wherein the compound of the Formula (I) is:

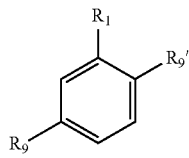
(I)

wherein:
R$_1$ is —(CH$_2$)$_a$Y or —CH=CH—(CH$_2$)$_p$Z;
Y is —SO$_3$H, —SO$_3^-$.X$^+$, —SO$_3$R$_3$, —PO$_3$H, —PO$_3^-$.X$^+$, —PO$_3$R$_3$;
Z is —SO$_3$H, —SO$_3^-$.X$^+$, —SO$_3$R$_3$, —PO$_3$H, —PO$_3^-$.X$^+$, —PO$_3$R$_3$, —CO$_2$H, —CO$_2^-$.X$^+$ or —CO$_2$R$_3$;
X$^+$ is an organic cation or an inorganic cation, such that the general charge of the compound is neutral;
R$_9$ and R$_{9'}$ are independently selected from —OH and —OR$_2$, wherein when R$_9$ and R$_{9'}$ are both —OR$_2$, then said R$_9$ and R$_{9'}$ can be the same or different;
R$_2$ is a substituted or unsubstituted alkyl group, a substituted or unsubstituted aryl group, a substituted or unsubstituted arylalkyl group, a substituted or unsubstituted alkylsulfonyl group, a substituted or unsubstituted arylsulfonyl group, a substituted or unsubstituted alkylarylsulfonyl group, a substituted or unsubstituted aryloalkysulfonyl group, a substituted or unsubstituted aryloxyalkyl group, a substituted or unsubstituted alkylcarbonyl group or an arylcarbonyl group, a carboxyl group, a substituted or unsubstituted alkoxycarbonyl group, a substituted or unsubstituted carboxyalkyl group, in particular —CH$_2$—COOH, or a substituted or unsubstituted alkoxy- aryloxy- arylalkoxy- or alkylaryloxy-carbonylalkyl, in particular —CH$_2$—COOR$_3$;
R$_3$ is a substituted or unsubstituted alkyl group or a substituted or unsubstituted aryl group,
a is number selected from 0, 1, 2, 3, 4, 5 and 6;
p is an integer selected from 0, 1, 2, 3, 4, 5 and 6,
with the proviso that when Y is —SO$_3$H, —SO$_3^-$.X$^1$ or —SO$_3$R$_3$ then R$_9$ and R$_{9'}$ are independently selected from –OH and —OR$_2$, wherein at least one of R$_9$ and R$_{9'}$ is a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In a particular embodiment, 2,5-dihydroxybenzene derivatives of the invention or any of the pharmaceutically acceptable salts thereof are those that are represented by Formula (I) comprising dobesilate ester derivatives and the pharmaceutically acceptable salts thereof for the treatment of dermatitis.

More particularly, the dermatitis is selected from the group consisting of actinic dermatitis, allergic contact dermatitis, atopic dermatitis, carcinomatous dermatitis, contact dermatitis, diaper dermatitis, stasis dermatitis, neurodermatitis, dermatomyositis and radiation-induced dermatitis.

The X$^+$ cation in the compound of Formula (I) may be any physiologically acceptable cation known in the art, that includes but is not limited to those described in P. Heinrich Stahl, Camille G. Wermuth (eds.), "Handbook of Pharmaceutical Salts Properties, Selections and Use", Verlag Helvetica Chimica Acta, Zurich, Switzerland, Wiley-VCH, Weinheim, Germany, 2002.

The X$^+$ cation is typically selected in such a way that the general charge of Formula (I) is neutral.

In a particular embodiment of the invention R1 is —(CH$_2$)$_a$Y or —CH=CH—(CH$_2$)$_p$Y. More particularly, Y is selected from —SO$_3$H, —SO$_3^-$.X$^+$, and —SO$_3$R$_3$.

In another particular embodiment of the invention, R$_3$ is selected from methyl, ethyl, isopropyl or C$_6$H$_5$—, more preferably from methyl and ethyl.

In another particular embodiment, R$_1$ is —(CH$_2$)$_a$Y or —CH=CH—(CH$_2$)$_p$Y.

In another particular embodiment, at least one of R$_9$ and R$_{9'}$ are, independently, a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In another particular embodiment, R$_2$ is selected from methylcarbonyl, phenylsulfonyl, 4-methylphenylsulfonyl, benzylsulfonyl, benzyl and phenyl In another particular embodiment, R$_2$ is selected from methylcarbonyl, phenylsulfonyl, 4-methylphenylsulfonyl, benzylsulfonyl, benzyl, and phenyl.

In another particular embodiment of the invention, R$_2$ is selected from acetyl (—C(O)CH$_3$), tosyl (—SO$_2$—C$_6$H$_4$—CH$_3$) or p-chlorophenoxyisobutyryl (—C(O)—C(CH$_3$)$_2$—O—C6H$_4$Cl).

In a preferred embodiment of the invention, the inorganic cation is sodium, potassium, lithium, calcium, or magnesium.

In another preferred embodiment of the invention, the organic cation is [NH$_{4-p}$R$_p$]$^+$: wherein p is an integer between 0 and 4 and R is an alkyl group having one to six carbon atoms such as, for example, methyl, ethyl, n-propyl, i-propyl, t-butyl or n-pentyl.

In another preferred embodiment of the invention, the organic cation is the diethylamine [H$_2$N$^+$(C$_2$H$_5$)$_2$], piperazine or pyridine group.

In another preferred embodiment of the invention, the compound of Formula (I) and acceptable salts thereof are:

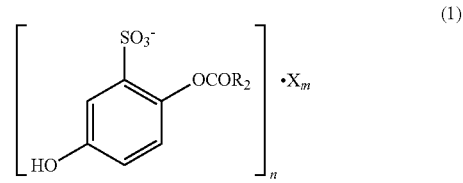
(1)

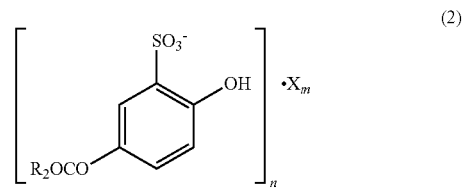
(2)

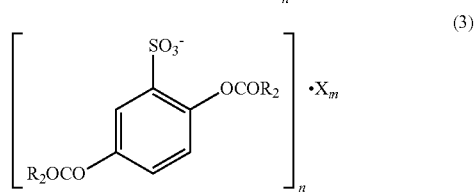
(3)

(4)
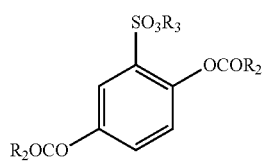
(5)
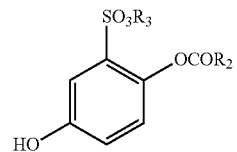
(6)
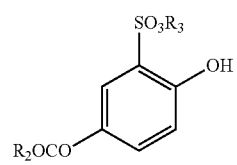
(7)
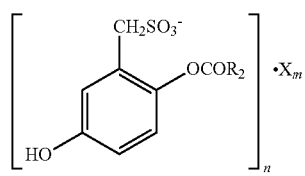
(8)
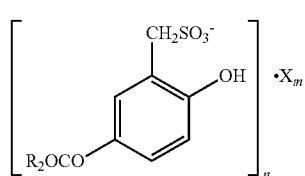
(9)
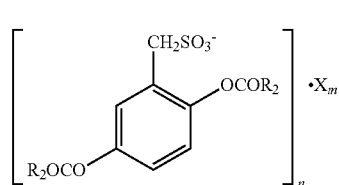
(10)
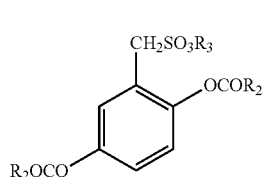
(11)
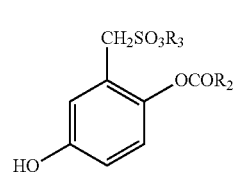
(12)
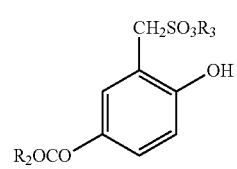
(13)
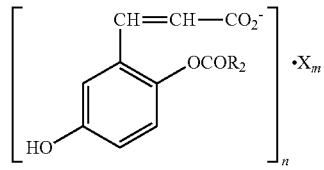
(14)
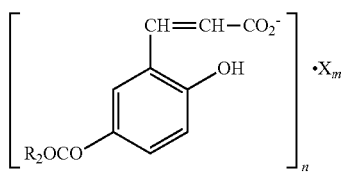
(15)
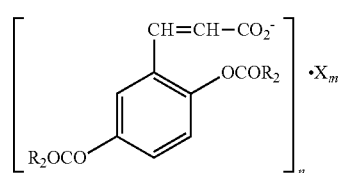
(16)
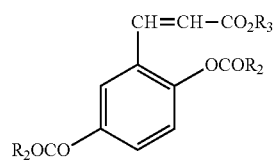
(17)
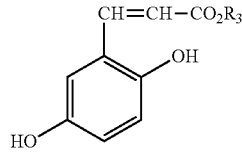
(18)
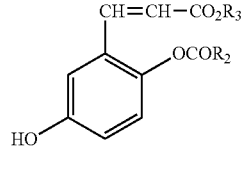
(19)
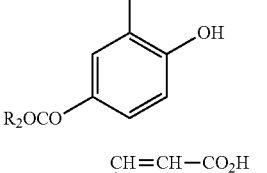
(20)
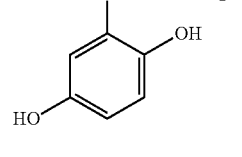
wherein:
n is a number selected from 1 and 2;
m is a number selected from 1 and 2; and
X, $R_2$ and $R_3$ are as defined in the present invention.
In a more preferred embodiment of the invention, the compound of Formula I is:
5-hydroxy-2-{[(4-methylphenyl)sulfonyl]oxy}benzenesulfonic acid;
2-hydroxy-5-{[(4-methylphenyl)sulfonyl]oxy}benzenesulfonic acid;

2,5-bis{[(4-methylphenyl)sulfonyl]oxy}benzenesulfonic acid;
2-(acetyloxy)-5-hydroxybenzenesulfonic acid;
5-(acetyloxy)-2-hydroxybenzenesulfonic acid;
2,5-bis(acetyloxy)benzenesulfonic acid;
5-hydroxy-2-{[(4-methylphenyl)sulfonyl]oxy}benzenehomosulfonic acid;
2-hydroxy-5-{[(4-methylphenyl)sulfonyl]oxy}benzenehomosulfonic acid;
2,5-bis{[(4-methylphenyl)sulfonyl]oxy}benzenehomosulfonic acid;
2-(acetyloxy)-5-hydroxybenzenehomosulfonic acid;
5-(acetyloxy)-2-hydroxybenzenehomosulfonic acid;
2,5-bis(acetyloxy)benzenehomosulfonic acid;
3-(2,5-dihydroxyphenyl)-2-propenoic acid (2,5-dihydroxycinnamic acid);
3-(5-hydroxy-2-{[(4-methylphenyl)sulfonyl]oxy}phenyl)-2-propenoic acid;
3-(2-hydroxy-5-{[(4-methylphenyl)sulfonyl]oxy}phenyl)-2-propenoic acid;
3-(2,5-bis{[(4-methylphenyl)sulfonyl]oxy}phenyl)-2-propenoic acid;
3-(2-(acetyloxy)-5-hydroxyphenyl)-2-propenoic acid;
3-(5-(acetyloxy)-2-hydroxyphenyl)-2-propenoic acid;
3-(2,5-bis(acetyloxy)phenyl)-2-propenoic acid;
3-(2-(benzyloxy)-5-hydroxyphenyl)-2-propenoic acid;
3-(5-(benzyloxy)-2-hydroxyphenyl)-2-propenoic acid;
3-(2,5-bis(benzyloxy)phenyl)-2-propenoic acid;
and pharmaceutically acceptable salts, solvates and prodrugs thereof.

Particularly preferred are the compounds 2-(acetyloxy)-5-hydroxybenzenesulfonic acid; 5-(acetyloxy)-2-hydroxybenzenesulfonic acid and 2,5-bis(acetyloxy)benzenesulfonic acid.

2,5-dihydroxybenzene derivatives may be optionally used combined with each other. In this manner and as an example, it is possible to combine a dobesilate ester derivative with a homodobesilate ester derivative, and the like in the same or in a different ratio. Said combinations may be in the same formulation or in formulations that would be used sequentially.

The compounds of Formula (I) may be synthesized by one skilled in the art using conventional and commercially available methods. The synthesis of the compounds of Formula (I) is disclosed in, for example, U.S. Pat. No. 5,082,941; and "The Merck Index" 13th. edition, Merck & Co., R. Railway, N.J., USA, 2001; U.S. Pat. Nos. 5,082,841, 4,814,110, 4,613,332 and 4,115,648; the disclosures which are incorporated herein by reference in their entirety.

Compounds of Formula (I) also may be in the form of solvates, particularly in the form of hydrates. The preparation of the compounds of Formula (I), as well as the solvates thereof may be carried out by one skilled in the art using conventional methods and commercially available reagents.

Even as it has been previously mentioned in one of the preferred embodiments with respect to the definition of $X^+$ cation, the scope of the present invention encompasses any salt thereof, especially any pharmaceutically acceptable salt of the compound. The please "pharmaceutically acceptable salts" includes metal salts or the addition salts that may be used in pharmaceutical forms. For example, the pharmaceutically acceptable salts of the compounds provided herein may be acid addition salts, base addition salts or metal salts and they may be synthesized from the parenteral compounds containing a base or acid residue using conventional chemical processes. Generally, those salts are prepared, for example, by the reaction of free base or acid forms of these compounds with a stoichiometric amount of the appropriate base or acid in water or in an organic solvent, or in a mixture of both. Generally, non aqueous mediums such as ether, ethyl acetate, ethanol, isopropanol or acetonitrile are preferred. The examples of acid addition salts include addition salts of mineral acids such as for example, hydrochloride, bromhydrate, iodide hydrate, sulfate, nitrate, phosphate, addition salts of organic acids such as, for example, acetate, maleate, fumarate, citrate, oxalate, succinate, tartrate, malate, mandelate, methanesulfonate and p-toluenesulfonate. The examples of alkali addition salts include inorganic salts such as, for example, ammonium salts and organic alkaline salts such as, for example, diethylamine, ethylenediamine, ethanolamine, N,N-dialkylenethanolamine, triethanolamine, glutamine and basic amino acid salts. The examples of metal salts include, for example, sodium, potassium, calcium, magnesium, aluminum, and lithium salts.

In some embodiments, the invention provides a composition comprising an ester derivative of a compound of Formula (I), especially an dobesilate ester derivative, such as 2-acetyloxy-5-hydroxybenzenesulfonic acid, 5-acetyloxy-2-hydroxybenzenesulfonic acid, or 2,5-bis-acetyloxybenzenesulfonic acid. In some embodiments, it will be desirable to formulate a composition of the invention with an active principle such as a dobesilate ester derivative, for example, wherein the ester derivative shows more therapeutic efficacy than the original compound in the treatment or prevention of a condition described herein. In other embodiments, the invention includes the use of a dobesilate ester derivative as a prodrug, for example, to treat a condition described herein, wherein the ester derivative is metabolized to the original compound in a patient to achieve therapeutic efficacy in the patient.

The phrase "pharmaceutically acceptable" refers to physiologically tolerable molecular entities and compositions which do not typically produce an allergic or similar adverse reaction, such as gastric upset, dizziness, and the like, when administered to a human. Preferably, as used herein, the term "pharmaceutically acceptable" means that it is approved by a regulatory agent of the Federal or a state government or listed in the U.S. Pharmacopeia or other generally recognized pharmacopoeia as suitable for use in animals, and more particularly, in humans.

It would be obvious to those skilled in the art that the scope of the present invention also encompasses salts that are not pharmaceutically acceptable as possible media to obtain pharmaceutically acceptable salts.

As used herein, the term "solvate" shall refer to any form of the active compound according to the invention that exhibits another molecule (most probably, a polar solvent) bound to it through a non-covalent bond. Examples of solvates include hydrates and alcoholates, preferably, $C_1$-$C_6$ alcoholates, for example, methanolate.

The pharmaceutically acceptable salts of Formula (I) may be prepared from organic or inorganic acids or basis by conventional methods through the reaction of the appropriate acid or base with the compound.

In a particular embodiment, 2,5-dihydroxybenzenic derivatives of the invention may be used optionally and jointly with at least one of the following therapeutic agents: diclofenac, T4 endonuclease, isotretinoin, acitretin, cidofoir, a corticosteroid, an antibiotic, an analgesic, an immunomodulator, including oral immunomodulator such as tacrolimus and pimecrolimus, and topical immunomodulators; an immunosuppressant, an anti-angiogenic, including anti-VEGF, anti-FGF, anti-EGF and anti-HGF; a leukotriene modifier, an aminosalicylate, an anesthetic, a non-steroidal anti-inflammatory, a therapy of the solubilized interleukin receptor, inhibitors of tyrosin-kinase receptors, protein kinase C inhibitors, and combinations of two or more thereof.

A medicament comprising a compound of formula (I) of the invention may be presented in any suitable form for administration, for example, for systemic, transdermal, oral, parenteral, buccal, nasal (e.g., by inhalation), topical, rectal, intravaginal, intraocular or optical administration; therefore, a medicament of the invention may include the acceptable pharmaceutical excipients or vehicles necessary to be formulated in the desired form of administration. In a preferred embodiment, the pharmaceutical composition is administered topically.

Thus, in one preferred aspect, the present invention refers to a method for the treatment and/or prophylaxis of dermatitis in a patient in need of the treatment and it comprises the administration to the patient of an effective amount of the described compounds and/or compositions of Formula (I).

The compounds of formula (I) may be optionally administered together with at least one therapeutic agent, such as, diclofenac, T4 endonuclease, isotretinoin, acitretin, cidofoir, a corticosteroid, an antibiotic, an analgesic, an immunomodulator, including oral immunomodulator such as tacrolimus and pimecrolimus, and topical immunomodulators; an immunosuppressant, an anti-angiogenic, including anti-VEGF, anti-FGF, anti-VEGF, anti-FGF, anti-HGF; a leukotriene modifier, an anesthetic, an aminosalicylate, an anesthetic, a non-steroidal anti-inflammatory, a therapy of the solubilized interleukin receptor, inhibitors of tyrosin-kinase receptors, protein kinase C inhibitors, and combinations of two or more thereof.

In other embodiments, the application of the 2,5-dihydroxybenzene compounds represented by Formula (I) may be made independently or, in a preferred aspect, simultaneously with the use of equivalent or different mixes of other 2,5-dihydroxybenzene compounds represented by Formula (I) (including pharmaceutically acceptable salts and esters) and these compounds may be in the same formulation or in independent formulations that would be simultaneously or sequentially administered.

In another aspect, the present invention refers to a cosmetic product comprising 2,5-dihydroxybenzene derivatives or any of the pharmaceutically acceptable salts thereof represented by Formula (I).

In an embodiment, the present invention refers to a cosmetic product that comprises 2,5-dihydroxybenzene derivatives or any of the pharmaceutically acceptable salts thereof represented by Formula (I) characterized in that the compound of Formula (I) is an ester derivative of 2,5-dihydroxybenzenesulfonic acid or pharmaceutically acceptable salts or esters thereof.

In another embodiment, the present invention refers to a cosmetic product that comprises 2,5-dihydroxybenzene derivatives or any of the pharmaceutically acceptable salts thereof represented by Formula (I) characterized in that the compound of Formula (I) is an ester derivative of 2,5-dihydroxybenzene homosulfonic acid or pharmaceutically acceptable salts or esters thereof.

In another embodiment, the present invention refers to a cosmetic product characterized in that the compound of Formula (I) is an ester derivative of 2,5-dihydroxybenzenesulfonic acid or the pharmaceutically acceptable salts or esters thereof characterized in that it consists of a formulation for dermatitis or seborrheic keratosis.

In another embodiment, the present invention refers to a cosmetic product according to any of the previous aspects characterized in that it is presented in the form of cream, ointment, unguent, microsomes, bandages, or patches.

In another embodiment, the present invention refers to a cosmetic product according to any of the previous aspects characterized in that it contains an amount of 5% of an ester derivative of 2,5-dihydroxybenzene sulfonic acid.

In another embodiment, the present invention refers to a cosmetic product according to any of the previous aspects characterized in that it comprises as excipients: cetyl alcohol (2.5%), stearyl alcohol (2.5%), liquid vaseline (30%), filante vaseline (20%), sorbitan monooleate (5%) and distilled water (q.s. to 100 g).

In another embodiment, the present invention refers to the use of 2,5-dihydroxybenzene derivatives or any of the pharmaceutically acceptable esters or salts thereof represented by Formula (I) to prepare a formulation intended to be cosmetically used.

In another embodiment, the present invention refers to a method for cosmetic or therapeutic treatment of dermatitis, comprising the administration to a patient of a composition comprising a compound of Formula (I).

In one embodiment, the present invention refers to the use of 2,5-dihydroxybenzene derivatives or any pharmaceutically acceptable esters or salts thereof represented by Formula (I) wherein the compound of Formula (I) is an ester derivative of 2,5-dihydroxybenzensulfonic acid or the salts or esters thereof, to prepare a drug or medicine intended for the cosmetic or therapeutic treatment of dermatitis.

In one embodiment, the present invention refers to the use of 2,5-dihydroxybenzene derivatives or any pharmaceutically acceptable esters or salts thereof represented by Formula (I) wherein the compound of Formula (I) is an ester derivative of 2,5-dihydroxybezene homosulfonic acid or the salts and esters thereof, to prepare a drug or medicine intended for the cosmetic or therapeutic treatment of dermatitis.

Another aspect of the present invention refers to a method for the cosmetic treatment of any of the diseases comprised in the following group: seborrheic keratosis, atopic dermatitis or contact dermatitis, comprising the administration to a patient of a composition comprising Formula (I), or the pharmaceutically acceptable salts or esters thereof.

Another aspect of the present invention refers to a method for therapeutic treatment of dermatitis, comprising the administration to a patient of a composition comprising Formula (I), or the pharmaceutically acceptable salts or esters thereof.

The duration of treatment will typically depend on the particular condition, its severity, the condition of the patient, and the like, and will readily be determined by one of skill in the art. Illustrative courses of therapy include 1 week, 2 weeks, 3 weeks, 4 weeks, 5 weeks, 6 weeks, 7 weeks, 8 weeks, 9 weeks, 10 weeks, 11 weeks, 12 weeks, 3.5 months, 4 months, 4.5 months, 5 months, 6 months, 9 months, a year, or longer as needed.

In treating a subject suffering from a disorder described herein, treatment may be continued until at least a 10% improvement is effected in a symptom associated with the condition. In other embodiments, treatment is continued until the subject in need of such treatment experiences an improvement of at least about 20%, at least about 30%, at least about 40%, preferably at least about 50%, preferably at least about 60%, more preferably at least about 70%, more preferably at least about 80%, even more preferably 90% or greater in a symptom associated with a disorder described herein.

In a particular embodiment of the invention, a compound of formula (I) is administered at least once per week. In other embodiments, a compound of formula (I) is administered at least once per day. In yet other embodiments, a compound of formula (I) is administered twice per day. In another particular embodiment, a compound of formula (I) is administered over a period of at least about one week. In other embodiments, a compound of formula (I) is administered over a period of at least about four weeks.

Therapeutic amounts can be empirically determined and will vary with the particular condition being treated, the subject, the particular formulation components, dosage form, and the like.

In a particular embodiment, a compound of formula (I) is present in a pharmaceutical composition in an amount of at least about 1% w/w. In other embodiments, a compound of formula (I) is present in a pharmaceutical composition in an amount of at least about 2.5% w/w, at least about 5% w/w, at least about 10% w/w, or at least about 15% w/w.

In another particular embodiment of the invention, the inventive 2,5-dihydroxybenzene compounds of Formula (I) may be administered topically in a formulation comprising from about 0.001% to about 30% (w/w) of the inventive 2,5-dihydroxybenzene compounds of Formula (I). In a preferred aspect of the invention, the inventive 2,5-dihydroxybenzene compounds of Formula (I) may be administered topically in a formulation comprising from about 0.01% to about 20% (w/w) of the inventive 2,5-dihydroxybenzene compounds of Formula (I). In another preferred aspect of the invention, the inventive 2,5-dihydroxybenzene compounds of Formula (I) may be administered topically in a formulation comprising from about 0.1% to about 15% (w/w) of the inventive 2,5-dihydroxybenzene compounds of Formula (I). In a preferred aspect of the invention, the inventive 2,5-dihydroxybenzene compounds of Formula (I) may be administered topically in a formulation comprising from about 0.5% to about 10% (w/w) of the inventive 2,5-dihydroxybenzene compounds of Formula (I). In another preferred aspect of the invention, the inventive 2,5-dihydroxybenzene compounds of Formula (I) may be administered topically in a formulation comprising from about 1% to about 5% (w/w) of the inventive 2,5-dihydroxybenzene compounds of Formula (I). In another preferred aspect of the invention, the inventive 2,5-dihydroxybenzene derivatives: of Formula (I) may be administered topically in a formulation comprising from about 2.5% to about 4% (w/w) of the inventive 2,5-dihydroxybenzene compounds of Formula (I). The topic formulation of the compounds comprised in the inventive 2,5-dihydroxybenzene compounds: of Formula (I) may be administered as a single dose once a day or in multiple doses several times a day. In a preferred aspect of the invention, the topical formulation which comprises 30%, 20%, 15%, 10%, 5%, 2.5%, 1%, 0.5%, 0.1% or 0.001% of the inventive 2,5 dihydroxybenzene compounds of Formula (I), is administered four times a day. In another preferred aspect of the invention, the topical formulation which comprises about 30%, 20%, 15%, 10%, 5%, 2.5%, 1%, 0.5%, 0.1% or 0.001% of the inventive 2,5 dihydroxybenzene compounds of Formula (I), is administered three times a day. In another preferred aspect of the invention, the topical formulation which comprises about 30%, 20%, 15%, 10%, 2.5%, 1%, 0.5%, 0.1% or 0.001% of the inventive 2,5 dihydroxybenzene compounds of Formula (I), is administered twice a day. In another preferred aspect of the invention, the topical formulation which comprises about 30%, 20%, 15%, 10%, 5%, 2.5%, 1%, 0.5%, 0.1% or 0.001% of the inventive 2,5 dihydroxybenzene compounds of Formula (I), is administered once a day.

Topical Compositions

The product of the present invention is useful for topical application on the skin. The compositions comprise an effective amount of the inventive compounds: of Formula (I), preferably from about 0.001 to 30%. Furthermore, the composition comprises a pharmaceutical acceptable vehicle. The appropriate vehicles remain in the place of application on the skin forming a continuous film resistant to water immersion and perspiration. Generally, the vehicle is organic and capable of containing the formulation of the invention in a diluted or dispersed form. Lotions, creams, solutions, gels and solids are the usual physical forms of the composition.

Topical application means depositing or spreading the compound and the compositions over the epidermic tissue (including skin and oral, gingival, nasal, etc. tissues).

Lotions

Lotions contain from about 0.001% to about 30% of the inventive compounds of Formula: (I) from 1% to 25% of an emollient and the appropriate amount of water. Examples of emollients are:

I. Hydrocarbon waxes and oils such as mineral oils, petrolatum, paraffin, ceresin, microcrystalline wax, polyethylene and perhydrosqualene.

II. Silicone oils such as dimethylpolysiloxanes, methylphenylpolysiloxanes and water-soluble and alcohol-soluble glycol-silicone copolymers.

III. Triglycerides, such as animal and vegetable fats and oils. Examples include, but are not limited to, castor oil, cod liver oil, corn oil, olive oil, almond oil, palm oil, sesame oil, cotton seed oil and soybean oil.

IV. Acetoglyceride esters, such as acetylated monoglycerides.

V. Ethoxylated glycerides, such as ethoxylated glycerol monostearate.

VI. Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristoyl lactate and cetyl lactate.

VII. Alkenyl esters of fatty acids having 10 to 20 carbon atoms. Examples thereof include, but are not limited to, oleyl myristate, oleyl stearate and oleyl oleate.

VIII. Fatty acids having 10 to 20 carbon atoms. Suitable examples include, but are not limited to, pelargonic, lauric, myristic, palmitic, stearic, isostearic, hydroxystearic, oleic, linoleic, ricinoleic, arachidonic, behenic and erucic acids.

IX. Fatty alcohols having 10 to 20 carbon atoms. Lauryl, myristoyl, palmitoyl, stearyl, isostearyl, hydroxystearyl, oleyl, ricinoleyl, behenyl, erucyl and 2-octyl dodecanol alcohols are appropriate examples of fatty alcohols.

X. Fatty alcohol ethers. Ethoxylated fatty alcohols having 10 to 20 carbon atoms include, but are not limited to, lauryl, cetyl, stearyl, isostearyl, oleyl and cholesterol alcohols having attached thereto from 1 to 50 ethylene oxide groups or 1 to 50 propylene oxide groups.

XI. Ether-esters, such as fatty acid esters of ethoxylated fatty alcohols.

XII. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleates, lanolin alcohols ricinoleate, acetate of lanolin alcohols ricinoleate, hydrogenolysis of lanolin, and liquid or semisolid lanolin absorption bases are illustrative examples of lanolin derived emollients.

XIII. Polyhydric alcohols and polyether derivatives. Propylene glycol, dipropylene polypropylene glycol 2000 and 4000, polyoxyethylene polypropylene glycols, glycerol, ethoxylated glycerol, propoxylated glycerol, sorbitol, ethoxylated sorbitol, hydroxypropyl sorbitol, polyethylene glycol 200-6000, methoxy polyethylene glycols 350, 550, 750, 2000, 5000, poly(ethylene oxide) homopolymers (100,000-5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), and polyoxypropylene derivatives of trimethylolpropane are suitable examples.

XIV. Polyhydric alcohol esters. Mono- and di-acyl esters of ethylene glycol, mono- and di-acyl esters of diethylene glycol, mono- and di-acyl esters of polyethylene glycol (200-6000), mono- and di-acyl esters of propylene glycol, polypropylene glycol 2000 monooleate, polypropylene glycol 2000 monostearate, ethoxylated propylene glycol monostearate, mono- and di-acyl esters of glycerol, poly-acyl esters of poly glycerol, ethoxylated glycerol monostearate, 1,3-butylene glycol monostearate, 1,3-butylene glycol distearate, acyl ester of polyoxyethylene polyol, acyl esters of sorbitan, and acyl esters of polyoxyethylene sorbitan are suitable examples.

XV. Waxes such as beeswax, spermaceti, myristoyl myristate and stearyl stearate, XVI. Beeswax derivatives, such as polyoxyethylene sorbitol beeswax. These are reaction products of beeswax with ethoxylated sorbitol of varying ethylene oxide content that form a mixture of ether-esters.

XVII. Vegetable waxes, including, but not limited to, carnauba and candelilla waxes, XVIII. Phospholipids such as lecithin and derivatives, XIX. Sterols. Examples include, but are not limited to, cholesterol and acyl esters of cholesterol.

XX. Amides, such as fatty acid amides, ethoxylated acyl amides and solid fatty acid alkanolamides.

The lotions of the invention would further contain from 1% to 30% of an emulsifier. The emulsifiers can be anionic, cationic or non-ionic. Examples of non-ionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbons in the alkyl chain condensed with 2 to 20 moles of ethylene oxide, mono- and di-acyl esters of ethylene glycol, wherein the fatty acid contains from 10 to 20 carbons, monoglycerides wherein the fatty acid contains from 10 to 20 carbons, diethylene glycol, polyethylene glycols of molecular weight 200 to 6000, polypropylene glycol of molecular weight 200 to 3000, glycerol, sorbitol, sorbitan, polyoxyethylene sorbitol, polyoxyethylene sorbitan and hydrophilic wax esters. Suitable anionic emulsifiers include, but are not limited to, fatty acids saponified (soaps) with potassium, sodium, or triethanolamine, wherein the fatty acid contains from 10 to 20 carbons. Other suitable anionic emulsifiers include, but are not limited to, alkali metals, ammonium or substituted ammonium with alkyl sulfates, alkyl arylsulfonates and alkyl ethoxy ether sulfonates having 10 to 30 carbons in the alkyl chain and from 1 to 50 ethylene oxide units. Suitable cationic emulsifiers include quaternary ammonium and morpholinium and pyridinium compounds.

Some emollients previously described also have emulsifying properties. When a lotion contains one of these emollients, an additional emulsifier is not needed, though it can be included in the formulation.

The balance of the composition is water. The lotions are formulated by simply admixing all of the components together. Preferably, the compounds of Formula I are dissolved in the emollient and the resulting mixture is added into the water. Optional components such as the emulsifier or common additives may be included in the composition. A common additive is a thickening agent included at a level of 1% to 30% by weight of the composition. Examples of suitable thickening agents are Cross-linked carboxypolymethylene polymers, methyl cellulose, polyethylene glycols, gums and bentonite.

Creams

The compositions of the present invention may be also formulated in the form of a cream. Creams contain torn 0.001% to 30% of the inventive compounds of Formula (I), from 5% to 50% of an emollient and the remainder is water. The emollients, as described above, can also be used in the cream formulation. Optionally, the cream may contain an emulsifier at a level from 3% to 50%. The previously described emulsifiers would also be adequate in this case.

Solutions

The compositions of the present invention may also be formulated in the form of a solution. Solutions contain from 0.001% to 30% of the inventive compounds: of Formula (I), and the adequate amount of an organic solvent. Organic substances useful as the solvent or a part of the solvent system are as follows: propylene glycol, polyethylene glycol (200-600), polypropylene glycol (425-2025), glycerine, sorbitol esters, 1,2,6-hexanetriol, ethanol, isopropanol, diethyl tartrate, butanediol, and mixtures thereof. Such solvent systems can also contain water. These compositions are applied on the skin in the faith of a solution, or solutions are formulated in the form of aerosol and applied on the skin as a spray. Compositions in the form of aerosol additionally contain from 25% to 80% of a suitable propellant. Examples of propellants include, but are not limited to: chlorinated, fluorinated and fluorochlorinated low molecular weight hydrocarbons. Nitrous oxide and carbon dioxide are also used as propellant gases. Enough quantity to expel the content of the cartridge is used.

Gels

The composition in the form of gel might be simply obtained by the addition of a suitable thickening agent to the composition in the form of a solution as described above. Suitable thickening agents have been described in the chapter referring to lotions.

Gel formulations contain from about 0.001% to about 30% of the compounds of Formula (I), 5% to 75% of a suitable organic solvent, 0.5% to 20% of a suitable thickening agent and the required amount of water.

Solids

The compositions in the present invention may also be formulated in solid form. Such forms have the shape of a bar intended for the application on the lips or other parts of the body. These compositions contain from about 0.001% to about 30% of the inventive compounds: of Formula (I), and from about 50% to about 98% of an emollient such as the one already described. The composition may be further contain from about 1% to about 20% of a suitable thickening agent, such as those already described, and, optionally, emulsifiers and water.

Additives usually found in topical compositions, such as preservatives (for example, methyl and ethyl paraben), dyes and perfumes may be included in any of the formulations described herein.

Application Method

The effective amount of compounds of Formula (I) used topically will vary according to the specific circumstances of application, the duration of exposure and similar considerations. Generally, the amount will vary from 0.01 microgram to 50 milligrams of the compounds of Formula (I), per square centimeter of the epidermis area. The amount of topical composition (the compounds of Formula (I) and the vehicle) applied on the affected area may be easily determined according to the amount of compounds of Formula (I) contained therein.

Kits

In yet other embodiments, the invention provides a kit or package comprising a compound of formula (I), in packaged form, accompanied by instructions for use. The compound of formula (I) may be packaged in any manner suitable for administration, so long as the packaging, when considered along with the instructions for administration, indicates the manner in which the compound of formula (I) is to be administered.

For example, a kit may comprise a compound of formula (I) in unit dosage form, along with instructions for use. For example, such instructions may indicate that administration of a compound of formula (I) is useful in the treatment of dermatitis. The compound of formula (I) may be packaged in any manner suitable for administration. For example, when the compound of formula (I) is in oral dosage form, e.g., is in the former of a coated tablet, then the kit may comprise a sealed container of coated tablets, blister strips containing the tablets, or the like.

Various embodiments according to the above may be readily envisioned, and would depend upon the particular dosage form, recommended dosage, intended patient population, and the like. The packaging may be in any form commonly employed for the packaging of pharmaceuticals, and may utilize any of a number of features such as different colors, wrapping, tamper-resistant packaging, blister packs or strips, and the like.

The following non-limiting examples further describe and enable one of ordinary Skill in the art to make and use the present invention.

EXAMPLES

Example 1

Effect of 2,5-Dihydroxybenzenesulfonate and the Ester Thereof, 2,5-Diacetoxybenzenesulfonate on Dermatitis Dermatitis was induced by the application of benzalkonium chloride, 5% solution (w/v) (1:5 olive oil:acetone) on the entire extent of the back part of the car (40 μL/ear) in anesthetized rats. Dermatitis was induced in both ears. In the assay of 2,5-dihydroxybenzenesulfonate (DHBS), a cream containing 5% of DHBS (w/w) was applied topically only on the back part of the right ear, 30 minutes after the application of benzalkonium chloride. Fifteen minutes later, 0.5% by weight of Evans blue dye solution (400 μL per animal) was injected into the jugular vein. This dye only stains in blue the areas of the skin that exhibit an alteration of the vascular permeability which enables the extravasation of the dye, as would correspond to a dermatitis process. Four hours after inducing dermatitis in both ears, the left ear of the studied rats (n=6) which had not been treated, exhibited a vast and intense blue stain, as shown in FIG. 1. Nevertheless, the right ear of all the rats treated with 5% DHBS exhibited a clearly smaller blue stain than the one in the respective left ear of each case (FIG. 1). Therefore it can be stated that topical application of 5% DHBS reduced the dermatitis extent.

Figure 2:
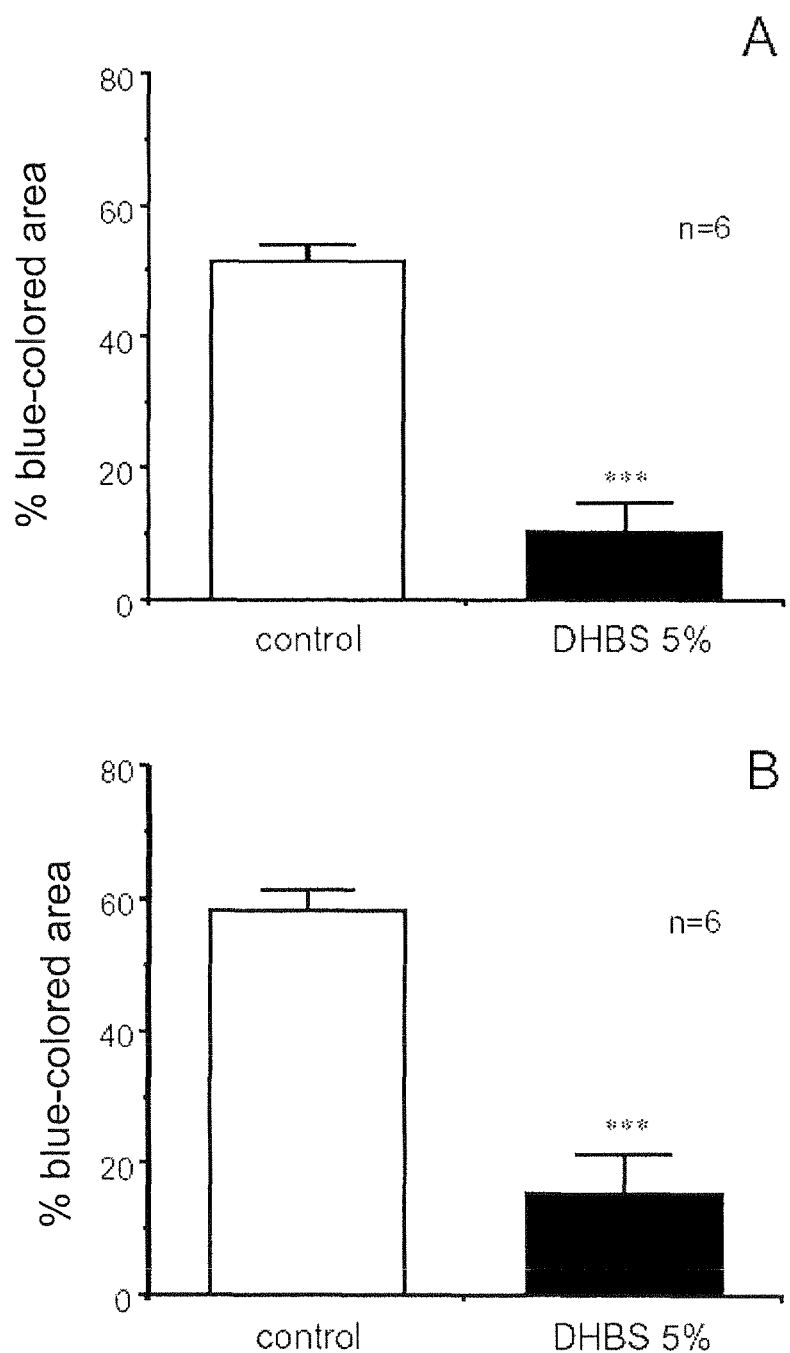
FIG. 2. Quantification of the inhibitory effect of 2,5-dihydroxybenzenesulnic acid (DHBS) on dermatitis induced by the application of benzalkonium chloride on the ears of the rats shown in FIG. 1. The abscissa axis represents the percentage of the blue-colored area compared to the total area of the ear, as a marker of the dermatitis extent. Data is expressed as the mean±SEM of the corresponding values of the six rats shown in FIG. 1. As shown in the graphs, topical application of 5% DHBS (black bars) significantly reduced dermatitis extent as observed 4 hours later (A) and 24 hours (B) after induction thereof.

This observation was confirmed upon quantification of dermatitis extent based on the area of the ear stained in blue with respect to the total area of the ear. Identically obtained photographs of the extended ears were processed in order to determine the stained area and the total area of the ear using a computer program to analyze images (Motic Image). The stained area of each ear was related to the total area to obtain the percentage of the ear affected by the dermatitis. The statistic analysis of the resulting values, 4 hours after the application of benzalkonium chloride on the treated and untreated ears, revealed that the treatment with cream containing DHBS at 5% by weight significantly reduced the percentage of the area stained in blue, as shown in FIG. 2A, thus, showing an inhibitory effect of DHBS on the development of dermatitis. 24 hours alter dermatitis induction (FIG. 2B), these values were very similar.

Figure 3:
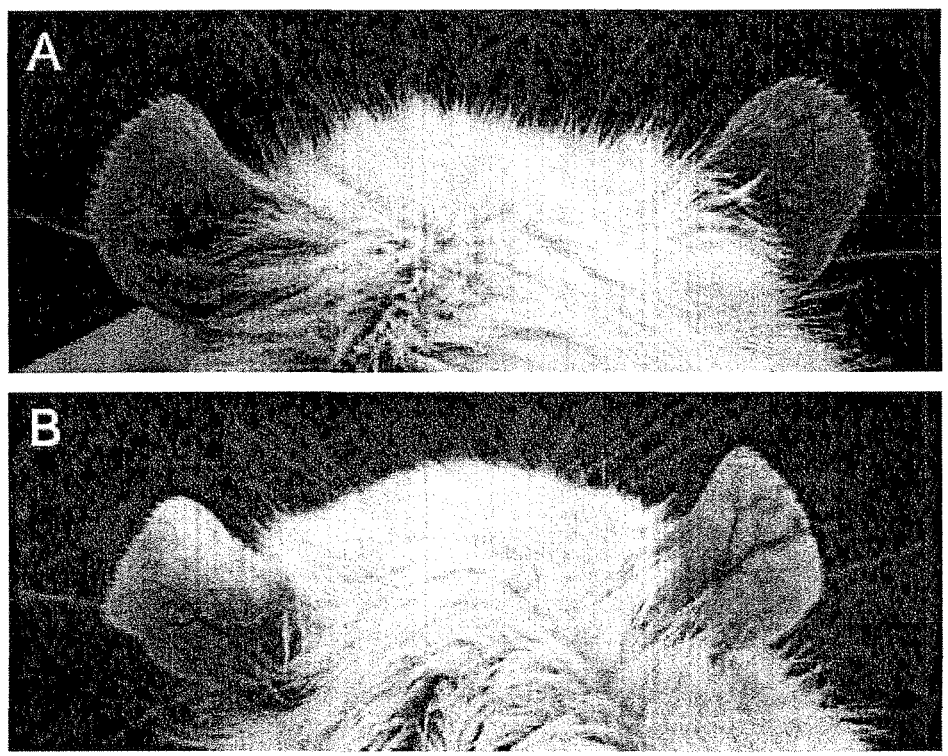
FIG. 3. Appearance of two rat ears on which benzalkonium chloride was applied to induce dermatitis. One of the rats (A), was treated topically with glycerol in both ears, while the other rat (B) was treated topically with a solution of glycerol containing 2.5% of 2,5-diacetoxybenzenesulfonic acid (DABS). The erythema caused by the dermatitis is milder in the mouse treated with DABS.
Figure 4:
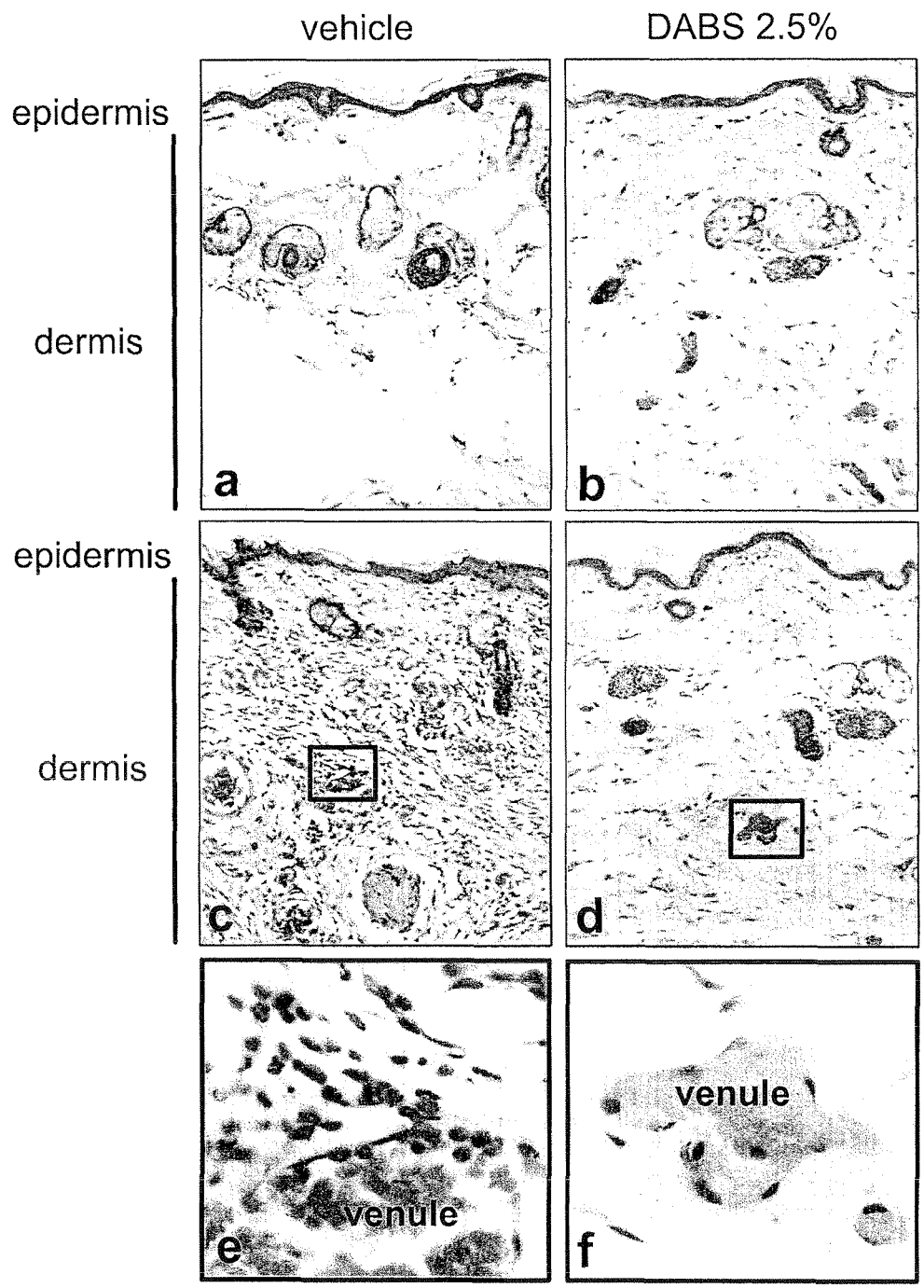
FIG. 4. Representative examples of the histological study of the effect of a topical treatment with 2.5% 2,5-diacetoxybenzenesulfonic acid (DABS) on the dermatitis induced by benzalkonium chloride on the ear of the rat. The microphotograph shows a clear tissular edema on the ear of a rat with dermatitis and treated only with the vehicle (anhydrous glycerol) (a). This edema is not observed in a rat with dermatitis but treated with 2.5% DABS in glycerol (b) in the ear treated with the vehicle, a considerable leukocyte infiltration in the tissue (c) may be observed, and it is noticeably milder in the ear of a rat treated topically with 2.5% DABS (d). The magnification of the area marked with a box in c and d shows that in the capillaries of the rat treated with vehicle there are granulocytes adhered to the endothelial cells that roll and extravasate to infiltrate the surrounding tissue (e), this is not observed in the vessels of the rat treated with DABS (f). The tissues were fixed 24 hours after dermatitis induction.

Using the same model, dermatitis was induced on both cars of two rats, following the same process described above. In this case, 30 minutes after the application of benzalkonium chloride, a rat was treated in both ears with a glycerol solution (FIG. 3A), while the other one was treated in both ears with a glycerol solution containing 2.5% (w/v) of 2,5-diacetoxybenzenesulfonate (DABS) (FIG. 3B). The topical treatment with DABS reduced benzalkonium chloride induced dermatitis, as evidenced by the fact that the ears of the rats treated with the vehicle (glycerol) exhibit a much more intense erythema than that corresponding to the rats treated with DABS. The histological study of these ears evidences that the topical treatment with 2.5% of DABS reduces the edema and the leukocyte infiltration (FIG. 4). The ears treated with DABS show a significant reduction of the presence of granulocytes adhered to the capillary endothelial cells, in its step previous to extravasation towards the subjacent tissue (FIGS. 4e and 4f).

In this same model (Hyun E et al. *Br J Pharmacol*, 2004), dermatitis induction has been associated to an increase in the myeloperoxidase (MPO) activity in the ear, as a marker of leukocyte infiltration in the tissue affected with dermatitis. Based on these evidences, the effect of hidroxybenzene derivatives on the activity of the MPO in the model described in this example was established. The MPO activity was determined in the ears of control rats (without dermatitis) and in ears on which dermatitis had been induced with benzalkonium chloride and had been treated with vehicle (anhydrous (glycerol), 5% DHBS cream or DABS 2.5% solution in glycerol. The ears were frozen in liquid nitrogen 24 hours after the induction of dermatitis and were kept at −80° C. until determination of MPO activity. To determine the MPO activity, the frozen ears were homogenized in phosphate buffer with 0.5% of hexadecyltrimethylammonium bromide. After several freezing/thawing sonication cycles, the samples were centrifuged at 13,000×g during 20 minutes at 4° C. H₂O₂ and O-dianisidine were added into the supernatants and the absorbance was measured at 460 nm in a spectrophotometer 1 hour after incubation at room temperature. The MPO activity is expressed as absorbance units per mg of tissue.

Figure 5:
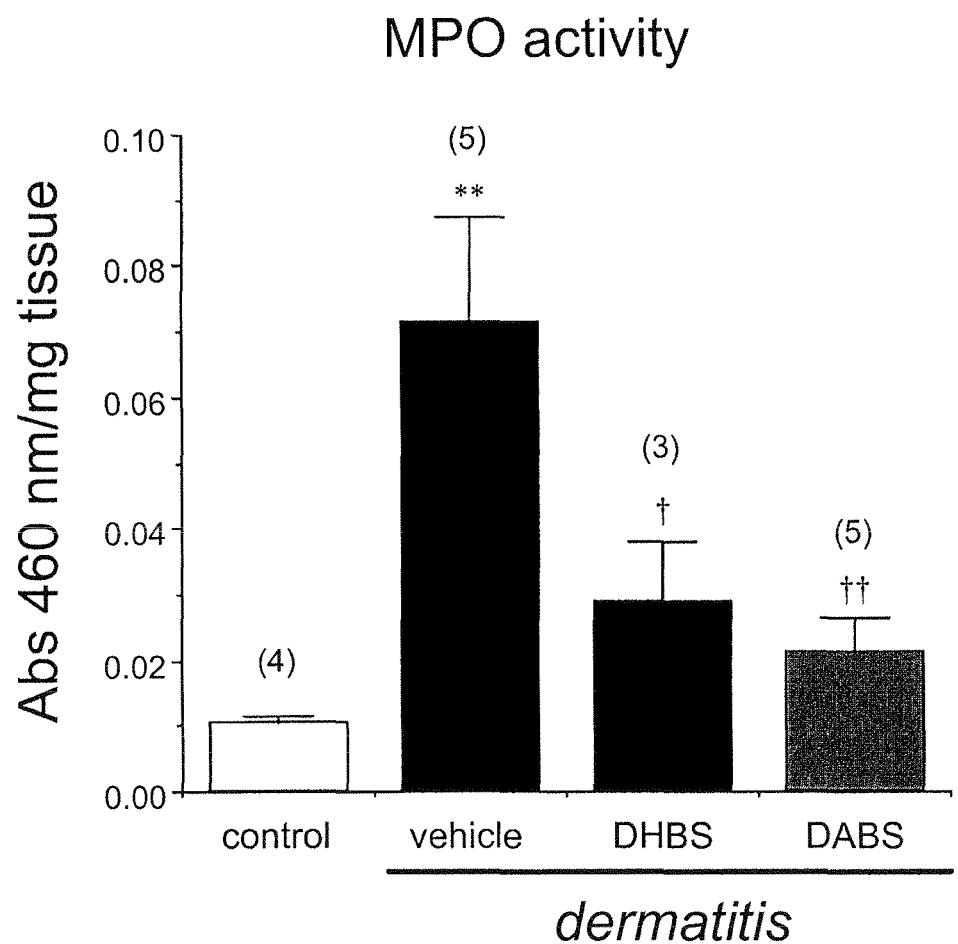
FIG. 5. Effect of the topical treatment with 2,5-dihydroxybenzenesulfonic acid (DHBS), 2,5-diacetoxybenzenesulfonic acid (DABS) or vehicle (anhydrous glycerol) over the increase of the myeloperoxidase (MPO) activity as a result of dermatitis induced by benzalkonium chloride on the ear of the rat. Once dermatitis was induced, the ears were treated with vehicle (anhydrous glycerol), a 5% DHBS cream, or with 2.5% DABS solution in anhydrous glycerol. Twenty-four hours after the dermatitis induction, the ears were removed and frozen. The control group corresponds to ears of rats in which dermatitis had not been induced. The MPO activity is expressed as the mean±SEM of the absorbance at 460 nm normalized by the mg of the tissue of the corresponding ear. The number of animals used in each group is stated between brackets. ** indicates $p<0.01$ vs. control, † $p<0.05$, †† $p<0.01$ vs. vehicle.

24 hours later, the dermatitis produces a significant increase in the MPO activity in the ear which is significantly reduced by the topical treatment with 5% DHBS (FIG. 5). The topical application of 2.5% of DABS also significantly reduces the increase of MPO activity caused by the dermatitis. In fact, when the DABS topical formulation contained half of the amount of active principle contained in the DHBS, its efficacy was slightly higher (FIG. 5).

This example shows the efficacy of the topical application of DHBS, and of the diacetylated form thereof, DABS, for the treatment of dermatitis in an animal model.

As the foregoing example illustrates, in certain embodiments, the esters of 2,5-dihydroxybenzene sulfonate described in the present invention surprisingly exert pharmacological actions of interest in the present invention by themselves, without needing to be first converted into 2,5-dihydroxybenzenesulfonate in order to exert such actions.

Example 2

Effect of Monoesters of 2,5-Dihydroxybenzenesulfonate on Dermatitis

Figure 6:
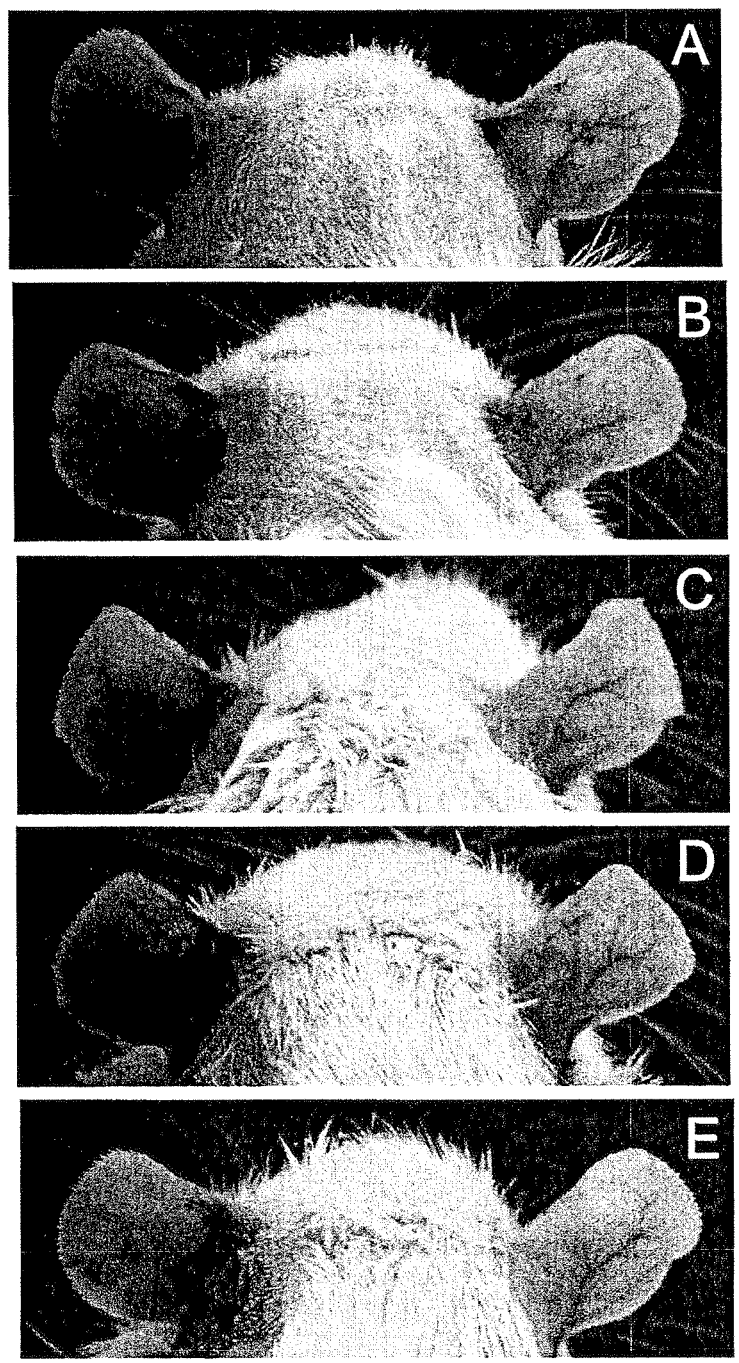
FIG. 6. Inhibitory effect of 2-acetoxy-5-hydroxybenzenesulfonic acid (2A-5HBS) on dermatitis induced by the application of benzalkonium chloride on the rat ears. Dermatitis was induced in both ears, and only the right ear was treated topically with a solution containing 5% 2A-5HBS in glycerol; the left ear was used as control. The intravenous injection of Evans blue dye revealed the extent of dermatitis in the ears. The application of the solution containing 5% 2A-5HBS remarkably reduced dye extravasation caused by the dermatitis, as shown in photographs (A-E) of the treated ears in the 5 rats that, 24 hours after dermatitis induction, exhibited a colored extent lower than untreated ears.
Figure 7:
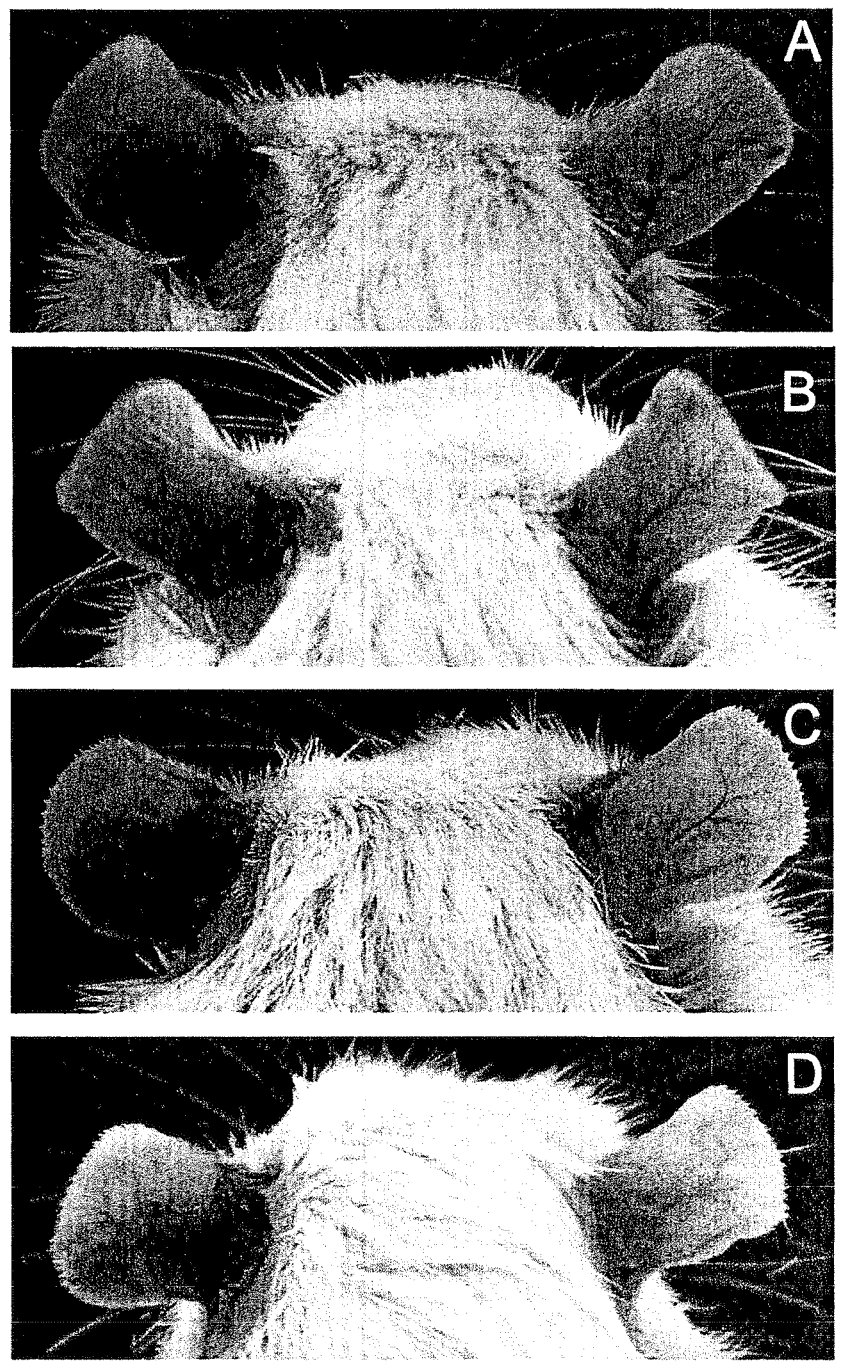
FIG. 7. Inhibitory effect of 5-acetoxy-2-hydroxybenzenesulfonic acid (5A-2HBS) on dermatitis induced by the application of benzalkonium chloride on the rat ears. Dermatitis was induced in both ears, and only the right ear was treated topically with a solution containing 5% 5A-2HBS in glycerol; the left ear was used as control. The intravenous injection of Evans blue dye revealed the extent of dermatitis in the ears. The application of the solution containing 5% 5A-2HBS remarkably reduced dye extravasation caused by the dermatitis, as shown in photographs (A-D) of the treated ears in the 4 rats that, 24 hours after dermatitis induction, exhibited a colored extent lower than untreated ears.

Using the same procedure as in the former example, dermatitis was induced by the application of benzalkonium chloride, 5% solution (w/v) (1:5 olive oil acetone) on the entire extent of the back part of the ear (40 μL/ear) in anesthetized rats. Dermatitis was induced in both ears. A cream containing 5% (w/v) of either 2-acetoxy-5-hydroxybenzenesulfonate (2A-5HBS) or 5-acetoxy-2-hydroxybenzenesulfonate (5A-2HBS) was applied topically only on the back part of the right ear, 30 minutes after the application of benzalkonium chloride. Fifteen minutes later, 0.5% (w/v) of Evans blue dye solution (400 μL per animal) was injected into the jugular vein. This dye only stains in blue the areas of the skin that exhibit an alteration of the vascular permeability which enables the extravasation of the dye, as would correspond to a dermatitis process. Twenty four hours after inducing dermatitis in both ears, the left ear of the studied rats (n=5) which had not been treated, exhibited a vast and intense blue stain, as shown in FIG. 6. Nevertheless, the right ear of all the rats treated with 5% 2A-5HBS exhibited a clearly smaller blue stain than the one in the respective left ear of each case (FIG. 6). In the same way, rats treated with 5% 5A-2HBS presented marked blue stain in the left (untreated) ears while the extent of the staining in the right (treated) ears was notably reduced (FIG. 7). Therefore, it can be stated that topical application of 5% 2A-5HBS and 5% 5A-2HBS reduced the dermatitis extent.

Figure 8:
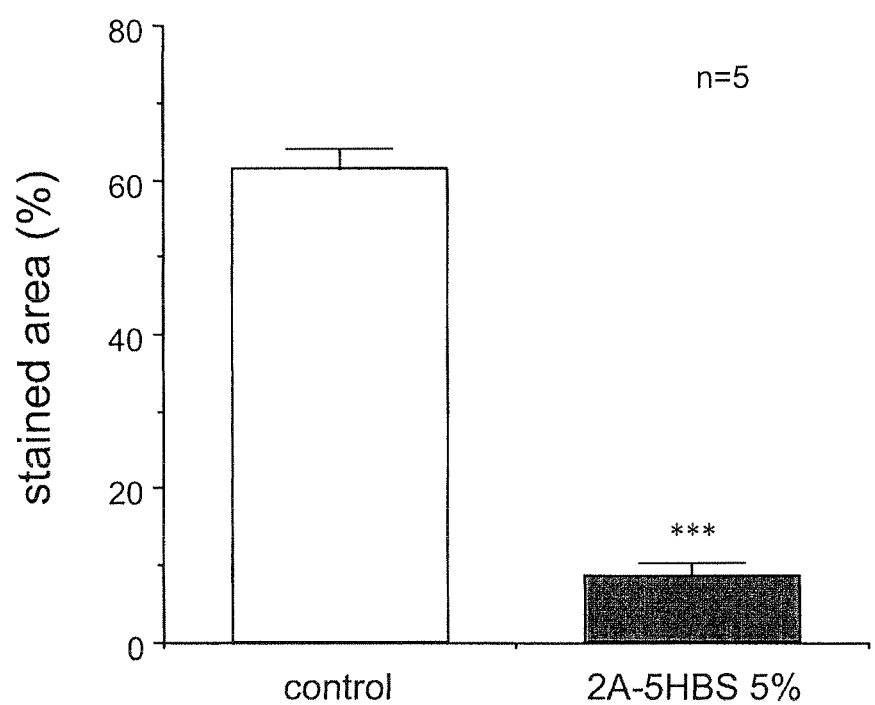
FIG. 8. Quantification of the inhibitory effect of 2-acetoxy-5-hydroxybenzenesulfonic acid (2A-5HBS) on dermatitis induced by the application of benzalkonium chloride on the ears of the rats shown in FIG. 6. The abscissa axis represents the percentage of the blue-colored area compared to the total area of the ear, as a marker of the dermatitis extent. Data are expressed as the mean±SEM of the corresponding values from the five rats shown in FIG. 6. As shown in the graphs, topical application of 5% 2A-5HBS (stripped bar) significantly reduced dermatitis extent 24 hours after induction thereof.
Figure 9:
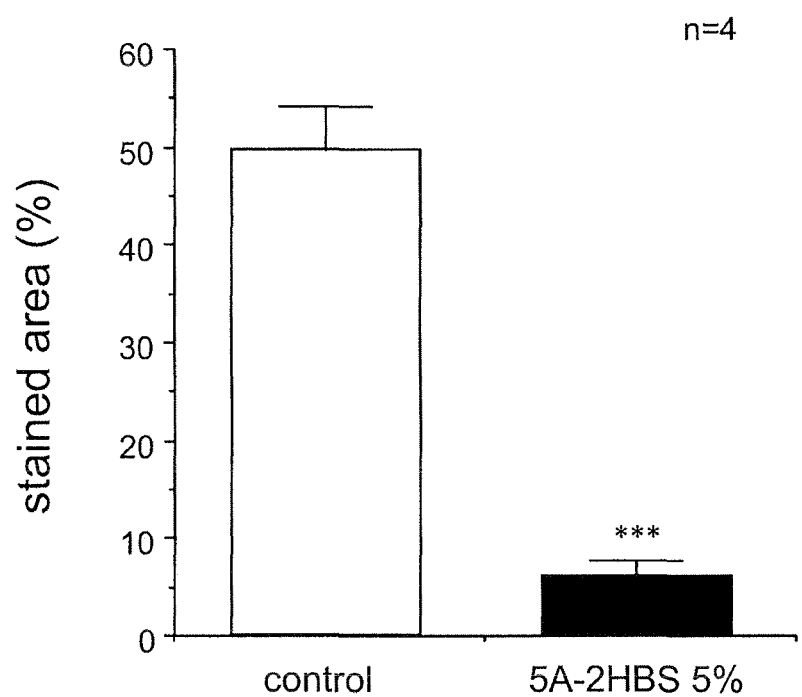
FIG. 9. Quantification of the inhibitory effect of 5-acetoxy-2-hydroxybenzenesulfonic acid (5A-2HBS) on dermatitis induced by the application of benzalkonium chloride on the ears of the rats shown in FIG. 7. The abscissa axis represents the percentage of the blue-colored area compared to the total area of the ear, as a marker of the dermatitis extent. Data are expressed as the mean±SEM of the corresponding values from the four rats shown in FIG. 7. As shown in the graphs, topical application of 5% 2A-5HBS (gray bar) significantly reduced dermatitis extent 24 hours after induction thereof.

This observation was confirmed upon quantification of dermatitis extent based on the area of the ear stained in blue with respect to the total area of the ear. Identically obtained photographs of the extended ears were processed in order to determine the stained area and the total area of the ear using a computer program to analyte images (Motic Image). The stained area of each ear was related to the total area to obtain the percentage of the ear affected by the dermatitis. The statistic analysis of the resulting values, 24 hours after the application of benzalkonium chloride on the treated and untreated ears, revealed that the treatment with 2A-5HBS solution at 5% by weight significantly reduced the percentage of the area stained in blue, as shown in FIG. 8, as well as did it the treatment with 5% (w/v) 5A-2HBS solution (FIG. 9) thus, showing an inhibitory effect of the monoesters of 2,5-dihydroxybenzesulfonate at positions 2 (2A-5HBS) or 5 (5A-2HBS) on the development of dermatitis.

Example 3

Analysis of the Structural Interaction of the Esters of 2,5-Dihydroxybenzenesulfonate with the Fibroblast Growth Factor-1 (FGF-1)

Figure 10:
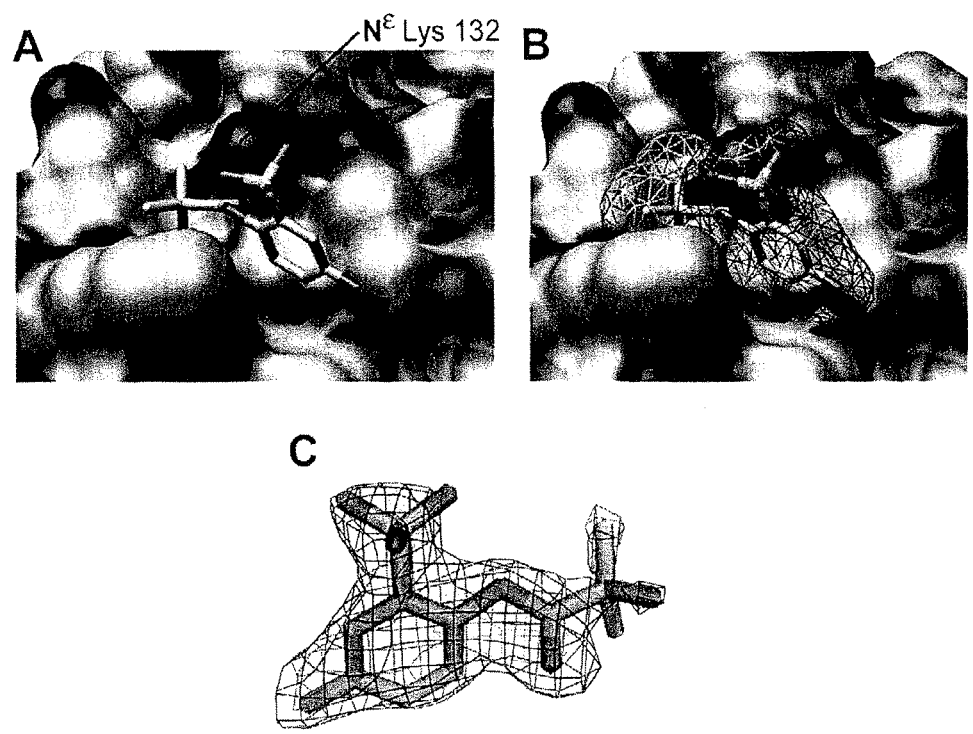
FIG. 10. Co-crystallized potassium 5-acetoxy-2-hydroxybenzenesulfonic acid with fibroblast growth factor-1. The electron density of the compound, contoured at $1\sigma$ to (panel C), enables the localization and recognition of the compound orientation regarding the protein (panels A and B), as well as the confirmation that the compound maintains the acetoxyl group in position 2 when it binds to the protein. The compound is located at a site very close to the site that, as described, is occupied by the 2,5-dihydroxybenzenesulfonic acid, which aromatic ring forms a cation-π bond with the $N\epsilon$ group of lysine 132, marked in panel A as reference. Panel B shows, in the form of a mesh, the Van der Waals volume of 2-acetoxy-5-hydroxybenzenesulfonic acid, overlapped to its representation in the form of rods. In panels A and B, the protein surface is colored according to its electrostatic potential (light grey: negative charge; dark grey: positive charge; white: lack of charge).
Figure 11:
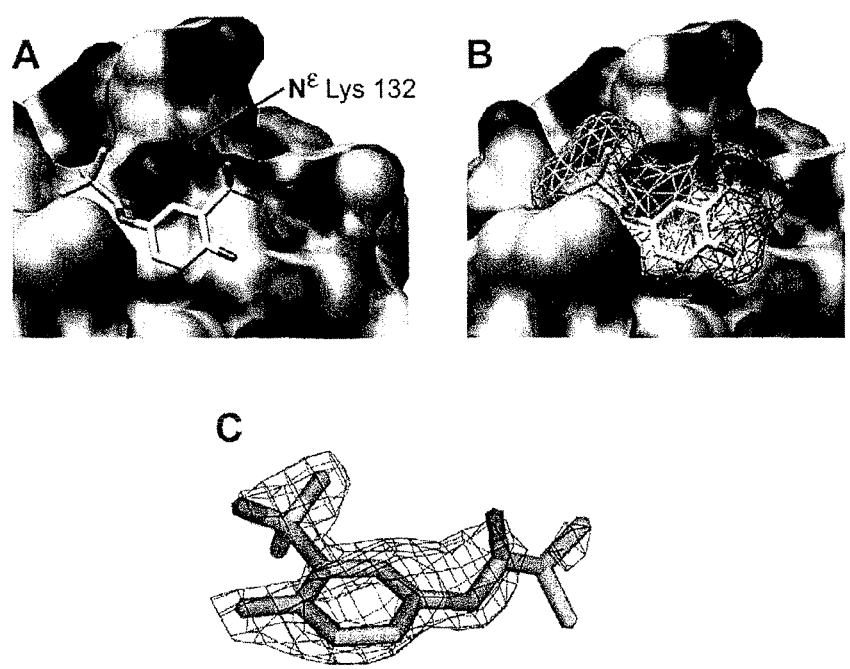
FIG. 11. Co-crystallized potassium 5-acetoxy-2-hydroxybenzenesulfonic acid with fibroblast growth factor-1. The electron density of the compound, contoured at $1\sigma$ (panel C), enables the localization and recognition of the compound orientation regarding the protein (panels A and B) as well as the confirmation that the compound maintains the acetoxyl group in position 5 when it binds to the protein. The compound is located at a site very close to the site that as described, is occupied by the 2,5-dihydroxybenzenesulfonic acid, which aromatic ring forms a cation-π bond with the $N^\epsilon$ group of lysine 132, marked in panel A as reference. Panel B shows, in the form of a mesh, the Van der Waals volume of 2-acetoxy-5-hydroxybenzenesulfonic acid, overlapped to its representation in the form of rods. In panels A and B, the protein surface is colored according to its electrostatic potential (light gray: negative charge; dark grey: positive charge; white: lack of charge).
Figure 12:
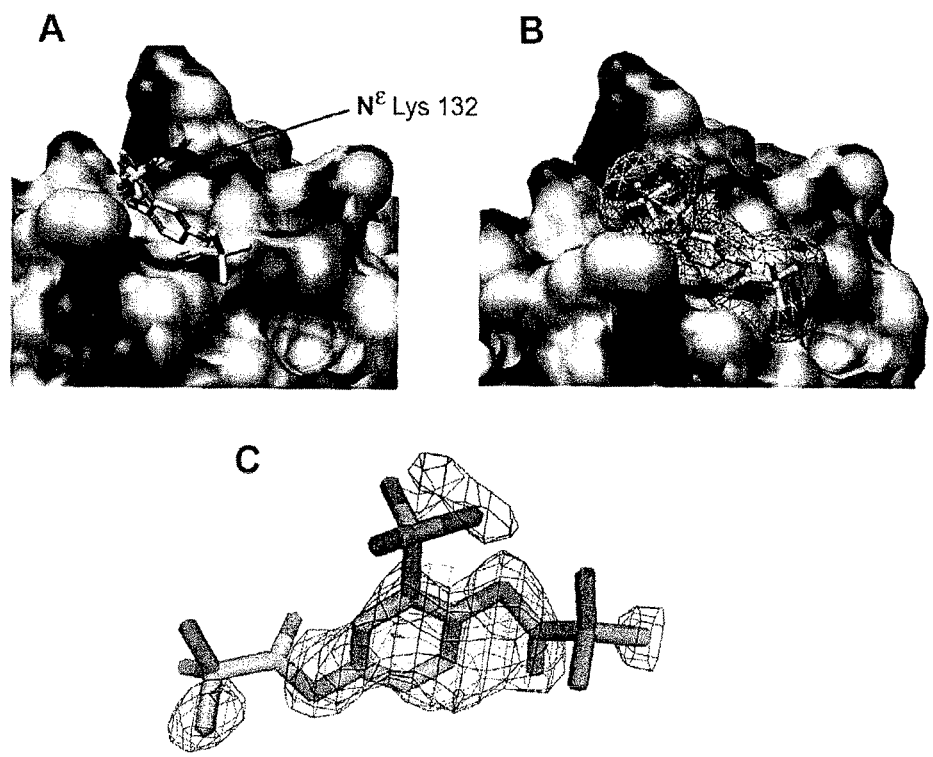
FIG. 12. Co-crystallized potassium 5-acetoxy-2-hydroxybenzenesulfonic acid with fibroblast growth factor-1. The electron density of the compound, contoured at $1\sigma$ (panel C), enables the localization and recognition of the compound orientation regarding the protein (panels A and B), as well as the confirmation that the compound maintains the acetoxyl group in position 2 when it binds to the protein. The compound is located at a site very close to the site that, as described, is occupied by the 2,5-dihydroxybenzenesulfonic acid, which aromatic ring forms a cation-π bond with the $N^\epsilon$ group of lysine 132, marked in panel A as reference. Panel B shows, in the form of a mesh, the Van der Waals volume of 2-acetoxy-5-hydroxybenzenesulfonic acid, overlapped to its representation in the form of rods. In panels A and B, the protein surface is colored according to its electrostatic potential (light grey: negative charge; dark grey: positive charge; white: lack of charge).

As of the diffraction from complex crystals of FGF-1: 2-acetoxy-5-hydroxybenzenesulfonic acid, FGF-1: 5-acetoxy-2-hydroxybenzenesulfonic acid and FGF-1; 2,5-diacetoxybenzenesulfonic acid, the complex structures were calculated and represented. In FIGS. 10, 11 and 12, representing the surface of the protein cleared according to its electrostatic potential (light grey: negative charge, dark grey: positive charge, white: areas with no charge), the interaction form of the 2-acetoxy-5-hydroxybenzenesulfonic acid, hydroxybenzenesulfonic acid and 2,5-diacetoxybenzenesulfonic acid, respectively, with the FGF-1 may be observed. The electronic density of the compound, contoured at 1 σ(FIGS. 10-12, panels C), enabled the localization and determination of the orientations of the compounds regarding the protein (FIGS. 10-12, panels A and B), as well as the confirmation that the compounds, keep the acetoxyl groups in positions 2, 5 and, 2 and 5, respectively, when they bind to the protein. The compounds are located at a site very close to the site that, as described, is occupied by the 2,5-dihydroxybenzenesulfonic acid, which aromatic ring forms a cation-π bond with the $N^\epsilon$ group of lysine 132, marked in FIGS. 10-12, panels A, as reference.

Each patent, patent application, and publication cited or described in the present application is hereby incorporated by reference in its entirety as if each individual patent, patent application, or publication was specifically and individually indicated to be incorporated by reference.

While specific embodiments of the subject invention have been discussed, the above specification is illustrative and not restrictive. One skilled in the art will appreciate that numerous changes and modifications can be made to the invention, and that such changes and modifications can be made without departing from the spirit and scope of the invention. The full scope of the invention should be determined by reference to the claims, along with their full scope of equivalents, and the specification, along with such variations.

What is claimed is:

1. A method for the treatment or prophylaxis of dermatitis, comprising administering topically to a subject in need thereof, an effective amount of a 2,5-dihydroxybenzene derivative represented by Formula (1) or a pharmaceutically acceptable salt, or solvate thereof, wherein the compound of Formula (1) is:

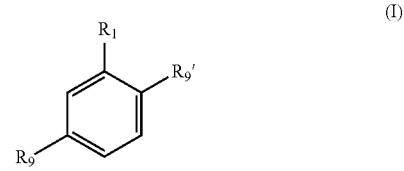

wherein:
R₁ is —CH═CH—(CH₂)$_p$Z;
Z is —CO₂R₃;
3 is methyl; and
p is 0.

2. The method of claim 1, wherein the compound of Formula (I) is selected from the group consisting of:
3-(2,5-dihydroxyphenyl)-2-propenoic acid;
3-(5-hydroxy-2-{[(4-methylphenyl)sulfonyl]oxy}phenyl)-2-propenoic acid;
3-(2-hydroxy-5-{[(4-methylphenyl)sulfonyl]oxy)}phenyl)-2-propenoic acid;
3-(2,5-bis{[(4-methylphenyl)sulfonyl]oxy}phenyl)-2-propenoic acid;
3-(2-(acetyloxy)-5-hydroxyphenyl)-2-propenoic acid;
3-(5-(acetyloxy)-2-hydroxyphenyl)-2-propenoic acid;
3-(2,5-bis(acetyloxy)phenyl)-2-propenoic acid;
3-(2-(benzyloxy)-5-hydroxyphenyl)-2-propenoic acid;
3-(5-(benzyloxy)-2-hydroxyphenyl)-2-propenoic acid;
3-(2,5-bis(benzyloxy)phenyl)-2-propenoic acid;
and pharmaceutically acceptable salts and solvates thereof.

3. The method of claim 1, wherein the dermatitis is selected from the group consisting of: actinic dermatitis, allergic contact dermatitis, atopic dermatitis, carcinomatous dermatitis, contact dermatitis, diaper dermatitis, stasis dermatitis, neurodermatitis, dermatomyositis and radiation-induced dermatitis.

4. The method of claim 1, further comprising administration of at least one additional therapeutic agent.

5. The method of claim 4, wherein the at least one additional therapeutic agent is selected from the group consisting of: diclofenac, T4 endonuclease, isotretinoin, acitretin, cidofoir, a corticosteroid, an antibiotic, an analgesic, an immunomodulator, including oral immunomodulator such as tacrolimus and pimecrolimus, and topical immunomodulators; an immunosuppressant, an anti-angiogenic; a leukotriene modifier, an aminosalicylate, an anesthetic, a non-steroidal anti-inflammatory, a modifier of a solubilized interleukin receptor, an inhibitor of a tyrosine-kinase receptor, a protein kinase C inhibitor, and a combination of two or more thereof.

6. The method of claim 1, wherein the compound is administered at least once per week.

7. The method of claim 6, wherein the compound is administered at least once per day.

8. The method of claim 7, wherein the compound is administered at least twice per day.

9. The method of claim 1, wherein the compound is present in a pharmaceutical composition in an amount of at least about 1% w/w.

10. The method of claim 9, wherein the compound is present in a pharmaceutical composition in an amount of at least about 2.5% w/w.

11. The method of claim 10, wherein the compound is present in a pharmaceutical composition in an amount of at least about 5% w/w.

12. The method of claim 11, wherein the compound is present in a pharmaceutical composition in an amount of at least about 10% w/w.

13. The method of claim 12, wherein the compound is present in a pharmaceutical composition in an amount of at least about 15% w/w.

14. The method of claim 1, wherein the compound is administered over a period of at least about one week.

15. The method of claim 14, wherein the compound is administered over a period of at least about four weeks.

* * * * *